US011136613B2

(12) United States Patent
Davies et al.

(10) Patent No.: US 11,136,613 B2
(45) Date of Patent: Oct. 5, 2021

(54) ANTIBACTERIAL POLYPEPTIDE LIBRARIES AND METHODS FOR SCREENING THE SAME

(71) Applicants: BOARD OF REGENTS, THE UNIVERSITY OF TEXAS SYSTEM, Austin, TX (US); PRESIDENT AND FELLOWS OF HARVARD COLLEGE, Cambridge, MA (US)

(72) Inventors: Bryan William Davies, Austin, TX (US); Ashley Timberlake Tucker, Austin, TX (US); M. Stephen Trent, Cedar Park, TX (US)

(73) Assignees: BOARD OF REGENTS, THE UNIVERSITY OF TEXAS SYSTEM, Austin, TX (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 333 days.

(21) Appl. No.: 15/570,262

(22) PCT Filed: Apr. 29, 2016

(86) PCT No.: PCT/US2016/030109
§ 371 (c)(1),
(2) Date: Oct. 27, 2017

(87) PCT Pub. No.: WO2016/176573
PCT Pub. Date: Nov. 3, 2016

(65) Prior Publication Data
US 2018/0135095 A1    May 17, 2018

Related U.S. Application Data

(60) Provisional application No. 62/155,183, filed on Apr. 30, 2015.

(51) Int. Cl.
| | | |
|---|---|---|
| *C12Q 1/18* | (2006.01) |
| *C12Q 1/68* | (2018.01) |
| *C07K 14/00* | (2006.01) |
| *C12Q 1/04* | (2006.01) |
| *C12N 15/70* | (2006.01) |
| *C12N 15/74* | (2006.01) |
| *G01N 33/50* | (2006.01) |
| *A61P 31/04* | (2006.01) |
| *G01N 33/68* | (2006.01) |
| *C12N 15/10* | (2006.01) |
| *C12N 15/62* | (2006.01) |

(52) U.S. Cl.
CPC .............. *C12Q 1/18* (2013.01); *A61P 31/04* (2018.01); *C07K 14/00* (2013.01); *C12N 15/1037* (2013.01); *C12N 15/62* (2013.01); *C12N 15/70* (2013.01); *C12N 15/74* (2013.01); *C12Q 1/04* (2013.01); *C12Q 1/68* (2013.01); *G01N 33/5008* (2013.01); *G01N 33/5014* (2013.01); *G01N 33/68* (2013.01); *C07K 2319/02* (2013.01); *C07K 2319/035* (2013.01); *G01N 2500/10* (2013.01)

(58) Field of Classification Search
CPC ............... C12Q 1/68; C12Q 2525/143; C12N 15/1037
See application file for complete search history.

(56) References Cited

U.S. PATENT DOCUMENTS

| | | | |
|---|---|---|---|
| 4,918,162 | A | 4/1990 | Salmon et al. |
| 5,073,627 | A | 12/1991 | Curtis et al. |
| 5,081,030 | A | 1/1992 | Civin |
| 5,348,867 | A | 9/1994 | Georgiou et al. |
| 5,646,011 | A | 7/1997 | Yokoyama |
| 5,780,225 | A | 7/1998 | Wigler et al. |
| 5,789,208 | A | 8/1998 | Sharon |
| 5,866,344 | A | 2/1999 | Georgiou |
| 6,214,613 | B1 | 4/2001 | Higuchi et al. |
| 6,300,065 | B1 | 10/2001 | Kieke et al. |
| 6,423,538 | B1 | 7/2002 | Wittrup et al. |
| 6,482,411 | B1 | 11/2002 | Ahuja et al. |
| 7,691,383 | B2 | 4/2010 | Chakrabarty et al. |
| 8,530,635 | B2 | 9/2013 | Chakrabarty et al. |
| 9,107,881 | B2 | 8/2015 | Mehta et al. |
| 9,309,292 | B2 | 4/2016 | Hong et al. |
| 9,475,864 | B2 * | 10/2016 | Ram .................... A61K 39/095 |
| 2003/0036092 | A1 | 2/2003 | Iverson et al. |
| 2003/0100023 | A1 | 5/2003 | Iverson et al. |
| 2004/0072740 | A1 | 4/2004 | Iverson et al. |
| 2004/0116665 | A1 | 6/2004 | Berthet et al. |

(Continued)

FOREIGN PATENT DOCUMENTS

| | | |
|---|---|---|
| EP | 0095361 | 11/1983 |
| WO | WO 1993/010214 | 5/1993 |

(Continued)

OTHER PUBLICATIONS

Deeudom et al., Antonie van Leeuwenhoek 107:1107-1116, Feb. 2015 (Year: 2015).*

(Continued)

*Primary Examiner* — Antonio Galisteo Gonzalez
(74) *Attorney, Agent, or Firm* — Parker Highlander PLLC

(57) ABSTRACT

Compositions and methods for isolating polypeptides having antibiotic activity are provided. In some aspects, bacterial cell populations are provided that express a surface-displayed library of candidate polypeptide sequences under the control of an inducible promoter.

10 Claims, 11 Drawing Sheets

Specification includes a Sequence Listing.

(56) References Cited

U.S. PATENT DOCUMENTS

2006/0040269 A1 2/2006 Chakrabarty et al.
2007/0258954 A1 11/2007 Iverson et al.
2018/0119134 A1 5/2018 Davies

FOREIGN PATENT DOCUMENTS

WO     WO 94/18330     8/1994
WO     WO 95/15393     6/1995

OTHER PUBLICATIONS

Chen et al., "Fusion protein likers: property, design and functionality," *Adv. Drug Deliv. Rev.*, 65(10):1357-1369, 2013.
Fox, "Antimicrobial peptides stage a comeback," *Nat. Biotechnol.*, 31(5):379-82, 2013, erratum in: *Nat. Biotechnol.*, 31(12):1066, 2013.
Georgiou et al., "Display of beta-lactamase on the *Escherichia coli* surface: outer membrane phenotypes conferred by Lpp'-OmpA'-beta-lactamase fusions," *Protein Eng.*, 9(2):239-47, 1996.
Guralp et al., "From design to screening: a new antimicrobial peptide discovery pipeline," *PLoS One*, 8(3):e59035, 2013.
Hilpert et al., "High-throughput generation of small antibacterial peptides with improved activity," *Nat. Biotechnol.*, 23(8): 1008-1012, 2005.
International Preliminary Report on Patentability issued in corresponding PCT Application No. PCT/US2016/030109, dated Nov. 9, 2017.
International Search Report and Written Opinion issued in corresponding PCT Application No. PCT/US2016/030109, dated Sep. 19, 2016.
Kovacikova et al., "Overlapping binding sites for the virulence gene regulators AphA, AphB and cAMP-CRP at the Vibrio cholera tcpPH promoter," *Mol. Microbiol.*, 41(2):393-407, 2001.
Novagen, "pET-21a-d(+) Vectors," <URL:http://www.helmholtz-muenchen.de/fileadmin/PEPF/pET_vectors/pET-21a-d_MAP.pdf> retrieved Aug. 31, 2016, published Dec. 1998.
Shin et al., "Display multimeric antimicrobial peptides on the *Esherichia coli* cell surface and its application as whole-cell antibiotics," *PLoS One*, 8(3):e58997, 2013.
Blakely, Kim, Troy Ketela, and Jason Moffat. "Pooled lentiviral shRNA screening for functional genomics in mammalian cells." *Network Biology*. Humana Press, 2011. 161-182.
Boder, Eric T., and K. Dane Wittrup. "Yeast surface display for screening combinatorial polypeptide libraries." *Nature Biotechnology* 15.6 (1997): 553.
Breitling, Frank, et al. "A surface expression vector for antibody screening." *Gene* 104.2 (1991): 147-153.
Hansson, M., et al. "Expression of recombinant proteins on the surface of the coagulase-negative bacterium *Staphylococcus xylosus.*" *Journal of bacteriology* 174.13 (1992): 4239-4245.
Office Communication issued in U.S. Appl. No. 15/801,383, dated Aug. 29, 2019.
Wang, Lin-Xu, et al. "*Escherichia coli* surface display of single-chain antibody VRC01 against HIV-1 infection." *Virology* 475 (2015): 179-186.
Office Communication issued in U.S. Appl. No. 15/801,383, dated Feb. 24, 2020.

\* cited by examiner cell lysis

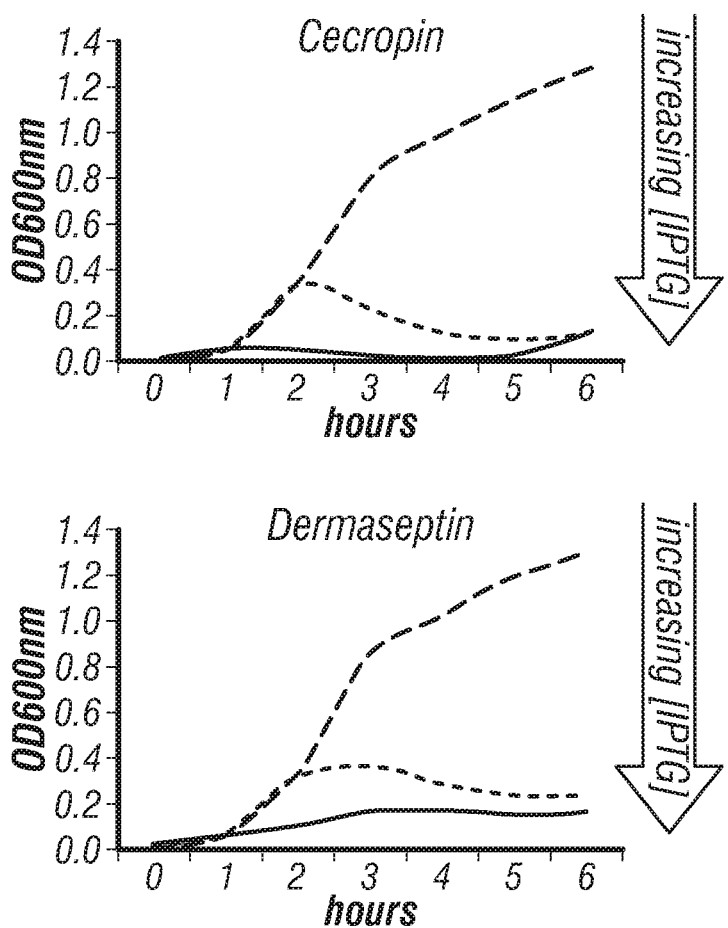
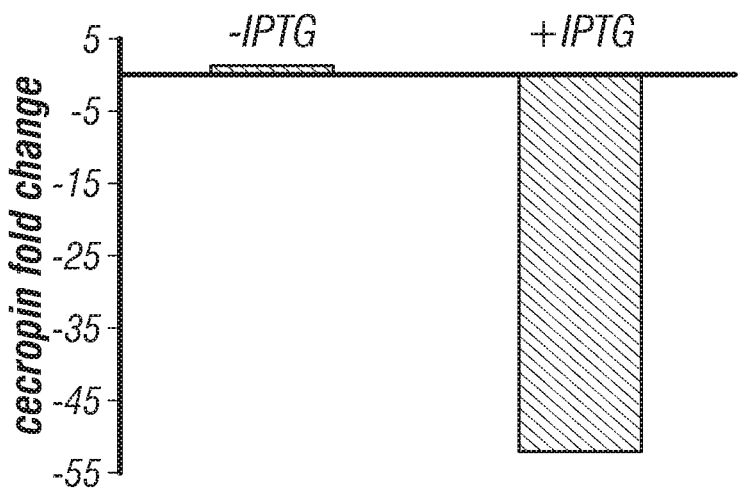
FIG. 2C
FIG. 2F

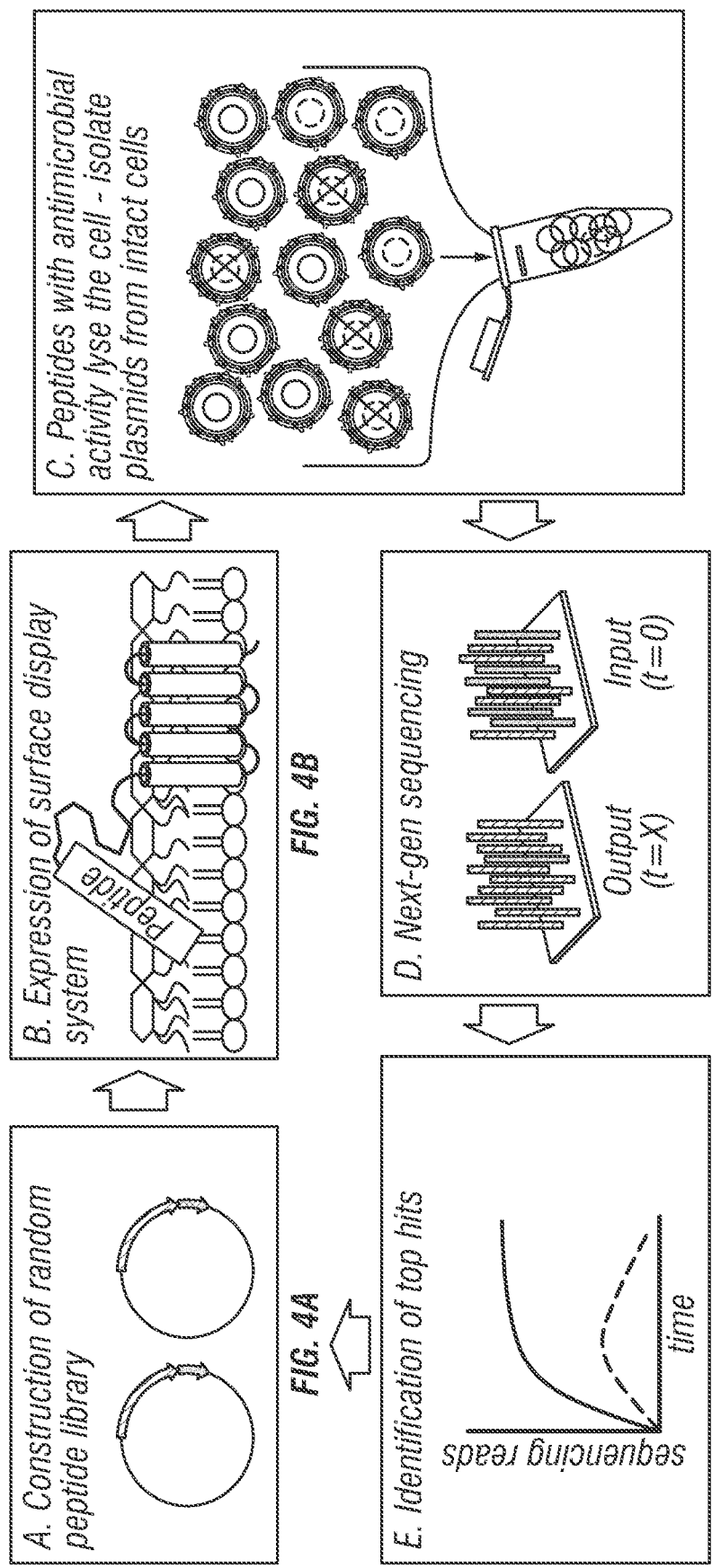

ANTIBACTERIAL POLYPEPTIDE LIBRARIES AND METHODS FOR SCREENING THE SAME

This application is a national phase application under 35 U.S.C. § 371 of International Application No. PCT/US2016/030109, filed Apr. 29, 2016, which claims the benefit of U.S. Provisional Patent Application No. 62/155,183, filed Apr. 30, 2015, the entirety of which is incorporated herein by reference.

INCORPORATION OF SEQUENCE LISTING

The sequence listing that is contained in the file named "UTSBP1061US ST25.txt", which is 36,157 bytes (as measured in Microsoft Windows®) and was created on Oct. 26, 2017, is filed herewith by electronic submission and is incorporated by reference herein.

BACKGROUND OF THE INVENTION

1. Field of the Invention

The present invention relates generally to the field of molecular biology, microbiology and medicine. More particularly, it concerns transgenic bacteria and method for identifying polypeptides having antibiotic activity.

2. Description of Related Art

Antibiotic resistant bacteria infect more than two million people annually in the United States, leading to more than 23,000 deaths and an additional $20 billion in health care costs (CDC, "Antibiotic Resistance Threats in the United States", 2013; Klevens et al., 2007). The rise of antibiotic resistance has surpassed the development of new antimicrobial agents; only two new classes of antibiotics have been discovered in the past 40 years, and bacteria have developed resistance to both (Clatworthy et al., 2007). At the current rate, the number of deaths attributed to antibiotic-resistant bacteria is projected to increase more than 10-fold over the next three decades (O'Neil, 2014).

Most antibiotics in use are small molecules derived from natural products such as penicillin produced from fungi (Fischbach et al., 2009). Efforts to identify new, or modify existing, small molecule antibiotics have been unable to slow the advance of antibiotic resistant bacteria. Antimicrobial peptides are an alternative class of antimicrobial agents with great potential to fight antibiotic resistance bacteria (Bahar et al., 2013; Otvos, 2008). Antimicrobial peptides are a fundamental component of the innate immune system and have been effective antimicrobials for billions of years, as opposed to the 1-2 decades enjoyed by most traditional small molecule antibiotics (Peschel et al., 2006; Wiesner et al., 2010). Antimicrobial peptides are polypeptides, typically 15 to 50 amino acids in length that disrupt the bacterial outer membrane and cause cell lysis. Antimicrobial peptides offer many benefits: broad-spectrum activity; fast action; and importantly, mechanisms of action with very low propensity for the development of resistance (Otvos, 2008; Man et al., 2006; Guilhelmelli et al., 2013; Upton et al., 2012). Lipopeptide antimicrobial peptides colistin and daptomycin are the drugs of last resort for multi-drug resistant Gram-negative and Gram-positive bacterial infections respectively, indicating the enormous potential of antimicrobial peptides to break the back of antimicrobial resistance (Gould et al., 2013; Bergen et al., 2012).

One of the largest hurdles to antimicrobial peptide development is the lack of effective and simple means to screen large numbers of peptides for antimicrobial activity (Cherkasov et al., 2009; Rathinakumar et al., 2010; Guralp et al., 2013). Current antimicrobial peptide screening is limited to small numbers (1,000-10,000) of short (<15 amino acids) peptides with defined chemistries (Hilpert et al., 2007). Peptides longer than 15 amino acids are generally more effective and stable antimicrobial agents under physiological conditions (Deslouches et al., 2005; Liu et al., 2007). Considering a small 6 amino acid peptide has 6.4× $10^7$ possible amino acid sequences, 10,000 peptides only covers ~0.02% of the potential pool of this small peptide's chemical space. The lack of high-throughput screening has prevented researchers from broadly testing peptide chemistry to define the most effective forms of antimicrobial peptides. Thus, there remains a need for methods of identifying and characterizing new, effective, polypeptides having antibiotic activity.

SUMMARY OF THE INVENTION

In a first embodiment the invention provides a method for identifying a polypeptide having antibiotic activity comprising: obtaining a population of bacterial cells, said cells comprising nucleic acid constructs encoding a fusion protein under the control of an inducible promoter, said fusion protein comprising a secretion signal sequence, a candidate polypeptide sequence, optionally, a linker sequence, and a bacterial membrane anchor sequence; inducing expression of the fusion protein in the bacterial cells; and identifying the candidate polypeptide sequences having antibiotic activity. In some aspects, identifying the candidate polypeptide sequences comprises identifying the sequences from bacterial cells that undergo lysis after the inducing step. In other aspects, identifying the candidate polypeptide sequences comprises separating intact cells from cells that are lysed. In further aspects, the method additionally comprises performing sequencing of the nucleic acid constructs in the population before said inducing step and performing sequencing from the intact cells after said inducing step to identify the candidate polypeptide sequences having antibiotic activity. In additional aspects, inducing expression of the fusion protein in the bacterial cells further comprises inoculating the bacterial cells into a test animal.

In a further embodiment there is provided a recombinant bacterial cell, comprising a heterologous nucleic acid construct encoding a fusion protein under the control of an inducible promoter, said fusion protein comprising: (i) a secretion signal sequence; (ii) a candidate polypeptide sequence; (iii) optionally, a linker sequence; and (iv) a bacterial membrane anchor sequence. In related embodiment there is provided a population of bacterial cells, said cells comprising a heterologous nucleic acid construct encoding a fusion protein under the control of an inducible promoter, said fusion protein comprising a secretion signal sequence, a candidate polypeptide sequence, an optional linker sequence, and a bacterial membrane anchor sequence, wherein said population collectively comprise a plurality of different candidate polypeptide sequences. In some aspects, the majority of the bacterial cells of the population comprise nucleic acid constructs encoding 1, 2 or 3 different candidate polypeptide sequences. In still further aspects, the majority of the bacterial cells of the population comprise nucleic acid constructs encoding no more than 2 different candidate polypeptide sequences.

In certain aspects, an encoded fusion protein of the embodiments comprises, from N- to C-terminus: (i) a secretion signal sequence; (ii) a candidate polypeptide sequence; (iii) an optional linker sequence; and (iv) a bacterial membrane anchor sequence. In other aspects, the encoded fusion protein comprises, from N- to C-terminus: (i) a secretion signal sequence; (iv) a bacterial membrane anchor sequence; (iii) an optional linker sequence; and (ii) a candidate polypeptide sequence. In some aspects the population of bacterial cells comprises nucleic acid constructs encoding 1,000 to 100,000, 500,000, 1,000,000, 5,000,000 or 10,000,000 different candidate polypeptide sequences.

In still further aspects, obtaining the population of bacterial cells comprises transforming a population of bacterial cells with said nucleic acid constructs, wherein the nucleic acid constructs encode a plurality of different candidate polypeptide sequences. In particular aspects, the method further comprises mutating the identified sequences having antibiotic activity to generate nucleic acid constructs with mutated candidate polypeptide sequences and identifying mutated candidate polypeptide sequences having antibiotic activity in accordance with the embodiment described above.

The bacterial cells may be gram positive or gram negative bacterial cells. In certain aspects, the bacterial cells comprise *Bacillus anthracis, Bordetella pertussis, Borrelia burgdorferi, Brucella abortus, Brucella canis, Brucella melitensis, Brucella suis, Burkholderia cepacia, Burkholderia pseudomallei, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli* (e.g., Enteropathogenic *E. coli*, Enterotoxigenic *E. coli* or *E. coli* O157:H7), *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumonia, Streptococcus pyogenes, Treponema pallidum, Vibrio cholera*, or *Yersinia pestis* cells. In some particular aspects, the bacterial cells are *E. coli*. In still further aspects, the bacterial cells are resistant to at least one antibiotic.

In still a further embodiment there is provided a recombinant DNA vector comprising a polypeptide coding sequence under the control of an inducible promoter, said polypeptide coding sequence comprising: (i) a sequence encoding a secretion signal sequence; (ii) a recombinant cloning site or a sequence encoding a candidate polypeptide; (iii) a sequence encoding a linker sequence; and (iv) a sequence encoding a bacterial membrane anchor sequence. In some aspects, the recombinant cloning site comprises a restriction endonuclease recognition sequence or a recombinase recognition site (e.g., a Cre recombinase recognition site). For example, in some cases, the recombinant cloning site comprises a multiple cloning site comprising a plurality of restriction endonuclease recognition sequences (e.g., 2, 3, 4, 5 or more different endonuclease recognition sequences). In preferred aspects, recombinant cloning site of the embodiments is arranged such that, after insertion of a candidate polypeptide coding sequence into the site, a fusion protein comprising sequence encoding the secretion signal, the candidate polypeptide and the membrane anchor is produced.

In a related embodiment there is provided a library of DNA vectors, each member of the library comprising a polypeptide coding sequence under the control of an inducible promoter, said polypeptide coding sequence comprising: (i) a sequence encoding a secretion signal sequence; (ii) a sequence encoding a candidate polypeptide; (iii) a sequence encoding a linker sequence; and (iv) a sequence encoding a bacterial membrane anchor sequence. For example, in some aspects, a library of the embodiments comprises DNA vectors encoding 1,000 to 100,000, 500, 000, 1,000,000, 5,000,000 or 10,000,000 different candidate polypeptide sequences.

Certain aspects of the embodiments concern fusion proteins comprising a secretion signal sequence, a candidate polypeptide sequence, an optional linker sequence, and a bacterial membrane anchor sequence. In particular aspects, the bacterial membrane anchor sequence can be a portion of a lipoprotein, an outer membrane protein or a component of the cell surface. In some aspects, the membrane anchor sequence is from a gram positive or gram negative bacteria. In certain aspects, the candidate polypeptide sequence may be from about 10, 15, 20, 25, 30, 35, 40, 45, 50, 100, 150 to 200 amino acids in length. In further aspects, the bacterial membrane anchor sequence comprises the membrane anchor sequence from OmpA. In some aspects, the bacterial membrane anchor sequence comprises a sequence at least 90%, 91%, 92%, 93%, 94%, 95%, 96%, 97%, 98%, 99% or 100% identical to SEQ ID NO: 1 (NPYVGFEMGYDWL-GRMPYKGSVENGAYKAQGVQLTAKLGYPITD-DLDIYTRLGG MVWRADTKSNVYGKNHDTGVSPVF-AGGVEYAITPEIATRLEYQWTNNIGDAHTIGT RPDN).

In still further aspects, the secretion signal of a fusion protein is from a gram positive or gram negative bacteria. In some specific aspects, the signal sequence is from murein lipoprotein (Lpp). In certain aspects, the secretion signal sequence comprises a sequence at least 90%, 91%, 92%, 93%, 94%, 95%, 96%, 97%, 98%, 99% or 100% identical to SEQ ID NO: 2 (MKATKLVLGAVILGSTLLAGCSSNAK-IDQ).

In yet still further aspects, a fusion protein of the embodiments comprises an optional linker sequence. In some aspects, the linker sequence may comprise two or more Gly positions or a poly Gly sequence. In certain aspects, a linker sequence comprises at least 5, 10, 15, 20, 25, 30, 35 or 40 amino acids. For example, the linker sequence can be from about 10 to 100 amino acids in length. In particular aspects, the linker sequence comprises a sequence at least 90%, 91%, 92%, 93%, 94%, 95%, 96%, 97%, 98%, 99% or 100% identical to SEQ ID NO: 3 (SQEPAAPAAEAT-PAAEAPASEAPAAEAAPADAAEAPAAGI). In other aspects, the linker sequence comprises at least two repeats of a sequence at 90% identical to SEQ ID NO: 3.

In still further aspects, a nucleic acid construct of the embodiments further comprises a transcription terminator after the sequence encoding the fusion protein. In certain aspects, the transcription terminator is the rrnB terminator. In yet still further aspects, the nucleic acid construct additionally comprises a selectable marker. The selectable marker may be a drug resistance marker.

In further aspects, the inducible promoter is a drug inducible promoter. In particular aspects, inducing expression of the fusion protein comprises applying a drug to the population, said drug inducing the promoter. In specific aspects, the drug inducible promoter is an Isopropyl β-D-1-thiogalactopyranoside (IPTG) inducible promoter.

In still yet further aspects, the inducible promoter is a promoter that is induced at a site of infection. In other aspects, the inducible promoter is a promoter from a bacterial virulence gene. In a specific aspect, the promoter may be *V. cholerae* virulence promoter. In certain aspects, the nucleic acid construct further comprises a selectable marker.

In still yet a further embodiment, the invention provides a laboratory animal comprising a bacterial cell or population of bacterial cells as described by the embodiments and aspects herein.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-F: (A) The antimicrobial peptide Cecropin P1 is attached to the OmpA surface display module by 0, 1×, or 2× low-complexity protein tethers (linkers). (B) Amount and rate of cecropin P1-dependent surface display cell lysis is enhanced by an increased tether length. The 2× tether-containing construct allows for the most efficient cell lysis. Overlapping curves labeled "Controls" include cells carrying all cecropin constructs without IPTG induction and cells with 2×HA constructs+/−IPTG. Cultures were induced with 0.1 mM IPTG. (C) Surface displayed antimicrobial peptide dermaseptin also causes cell lysis. The amount and rate of both cecropin P1 and dermaseptin-dependent surface display cell lysis is dependent on IPTG induction level. Cultures were induced with 0, 0.1 or 1.0 mM IPTG, indicated by increased shading of the graph plots. (D) The 2×-tether cecropin P1 surface display construct was induced with 0.1 mM IPTG in wild type *E. coli* W3110 or the isogenic antimicrobial peptide resistant mutant WD101. (E) *E. coli* expressing 2× tether+cecropin P1 or empty vector were co-cultured and grown+/−0.1 mM IPTG for 3 hours. The cultures were serially diluted in 10-fold increments and plated to determine colony-forming unit. (F) Plasmid was prepared from the co-culture experiment with or without 3 hours of 0.1 mM IPTG induction. qPCR analysis showed the level of cecropin P1 plasmid decreased ~50 fold relative to the control plasmid in the co-culture induced with IPTG for 3 h.

FIGS. 4A-E: Workflow for antimicrobial peptide identification using the peptide surface display platform of the embodiments.

DESCRIPTION OF ILLUSTRATIVE EMBODIMENTS

I. The Present Embodiments

Infections caused by bacteria with resistance to conventional antibiotics is a growing problem world-wide. Despite this, there is a dearth new antibiotic compounds in the drug development pipeline. Moreover, it has become increasingly apparent that resistance to small molecule antibiotics can be quickly developed and spread in bacterial populations. Polypeptide antibiotics offer a potential answer to this problem by providing novel antibiotics that may be less susceptible to the development of resistance. However, while current small molecule libraries used to identify lead therapeutic molecules typically contain 500,000 unique compounds (Hartigan 2010), there has previously been no such diverse library or screening method available for identifying polypeptide-based antibiotics.

Figure 1:
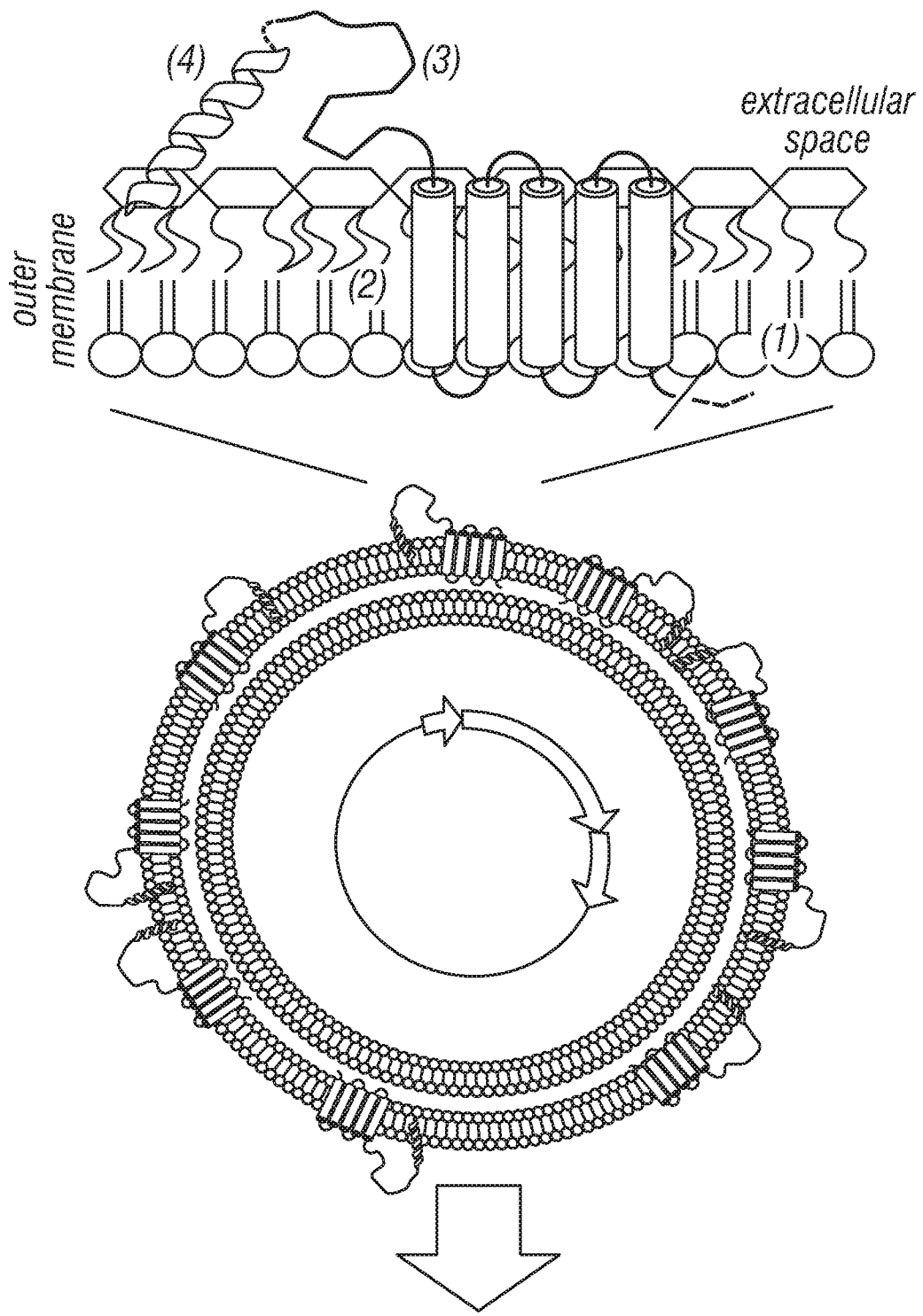
FIG. 1: Schematic show an example antimicrobial peptide surface display system comprised of (1) Lpp signal sequence, (2) OmpA transmembrane helices (membrane anchor), (3) flexible tether (linker), and (4) a C-terminal peptide (candidate polypeptide). Induction of the system leads to surface display of the C-terminal antimicrobial peptide and cell lysis, which eliminates the expressing bacterium from the population.
Figure 1:
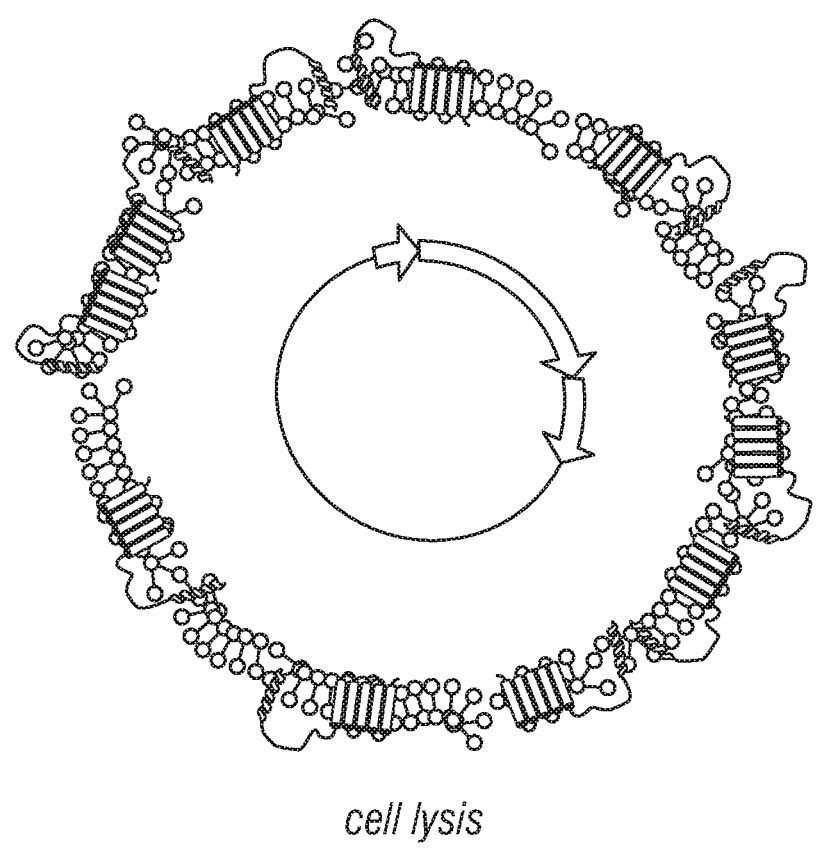
Figure 6:
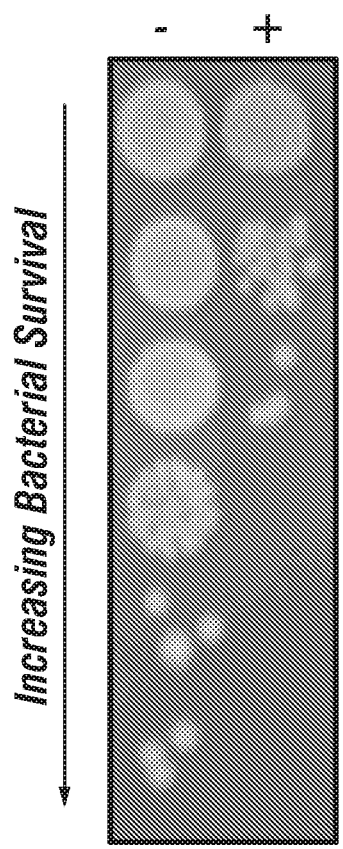
FIG. 6: An antibiotic-resistant bacterium was incubated with (+) or without (−) Peptide A.

Studies detailed herein demonstrate that by using a unique inducible surface display system, candidate antibiotic polypeptides can be rapidly identified and characterized. An example, of a surface display system of the embodiments is shown graphically in FIG. 1. Candidate antibiotic polypeptides are expressed in bacterial cells from an inducible promoter system and are fused with a secretion signal and an anchor polypeptide, that allows the candidate antibiotic sequence to be displayed in the surface of the expressing bacteria resulting in lysis of the cell only when the sequence has antibiotic activity. Using an *E. coli* model system, the inventors have shown that a known antimicrobial polypeptide (cecropin) can be, upon promoter induction, displayed on the surface of bacteria and selectively promote lysis only of the bacteria that display the polypeptide (see, FIG. 2). In some cases, it was found that the efficiently of cell lysis by antibiotic polypeptides could be enhanced by linking the candidate sequence with the anchor using a flexible linker (see, FIG. 2B). To assess the efficacy of the system in identifying new antibiotics, a library of candidate sequences was tested. As shown in FIG. 6, the methods were able to efficiently identify new polypeptides having significant antibiotic activity. In fact, one example sequence identified ("Peptide A") was shown to be more cytotoxic even than the positive control cecropin polypeptide. Moreover, as demonstrated by the data in FIG. 7, candidate polypeptides having a wide range of physical characteristics could be successfully screened and identified by the methods of the embodiments.

The methods provided herein address the need for libraries that may be used to screen for polypeptide antibiotics. In particular, the inventors have developed a high-through system for identifying and selecting polypeptide sequences that promote lysis of bacterial cells. Importantly, the system is able to identify polypeptides that operate on the exterior of the cell and do not, therefore, require additional modifications (i.e., to allow the polypeptides to enter into cells). However, despite the exterior display of library sequences, the system was surprisingly found to specifically promote lysis only of bacterial cells that express the antibiotic sequence. This new screening methodology can be adapted for use in a wide range of gram positive and gram negative bacterial systems and therefore can be used to identify new antibiotics specific for any bacterial pathogen of interest. Moreover, the methods detailed herein allow polypeptides to be selected from highly diverse libraries, which allows for large numbers of candidate antibiotics to be efficiently identified and characterized in a very short time span.

II. Nucleic Acid-Based Expression Systems

A wide range of nucleic acid-based expression systems may be used for the expression of candidate antibiotic polypeptides. For example, one embodiment of the invention involves transformation of bacteria with the coding sequences of fusion polypeptides comprising a candidate antibiotic polypeptide linked to a membrane anchor sequence and section signal. Numerous expression systems exist that comprise some or all of the sequence components discussed below.

Vectors may find use with the embodiments, for example, in the transformation of bacterial cells with a nucleic acid sequences encoding a candidate polypeptide which one wishes to screen for antibiotic activity. In one embodiment of the invention, an entire heterogeneous "library" of nucleic acid sequences encoding candidate polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, bacteriophages, and artificial chromosomes. However, in preferred aspects, vectors for use according to the embodiments are plasmid vectors, which do not integrate in the genome of host bacterial cells. An examples of such an expression system is the pET Expression System and an *E. coli* expression system. A plasmid-based inducible expression system for use in gram positive bacteria, such as *Staphylococcus aureus*, is likewise detailed in Liew et al., 2011, which is incorporated herein by reference. One of skill in the art may construct a vector through standard recombinant techniques, which are described in Maniatis et al., 1988 and Ausubel et al., 1994, both of which are incorporated herein by reference.

The term "expression vector" refers to a vector containing a nucleic acid sequence coding for at least part of a gene product capable of being transcribed and then translated into a polypeptide. Expression vectors can contain a variety of "control sequences," which refer to nucleic acid sequences necessary for the transcription and possibly translation of an operably linked coding sequence in a particular host organism (e.g., gram positive or gram negative bacteria). In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Preferably a promoter a promoter for use according to the embodiments is a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. Furthermore, it is contemplated that the control sequences that direct transcription and/or expression of sequences within non-nuclear organelles such as mitochondria, chloroplasts, and the like, can be employed as well.

In preferred aspects, a promoter (or promoter enhancer system) for use according to the embodiments is an inducible promoter that provides expression of a sequence based on an external stimulus. For example, the inducible promoter may be a promoter that provides expression only in the presence of a particular compound (e.g., IPTG), at a particular pH, or in specific environmental (e.g., lighting) conditions.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such an antibiotic resistance marker.

7. Fusion Polypeptides

As described above, in some aspects a vector of the embodiments comprises a sequence for expression, which comprises a fusion of a membrane anchor sequence and a candidate polypeptide sequence. Furthermore, in some aspects, the fusion polypeptide comprises a secretion signal that directs the fusion protein to the bacterial (outer) membrane. Optionally, the fusion polypeptide further comprises a linker positions between the candidate polypeptide sequence and the membrane anchor sequence.

a. Signal Sequences

In some aspects, a fusion polypeptide of the embodiments comprises a signal sequence that targets the fusion polypeptide to the membrane (and may be cleaved away from the fusion). In certain aspects, the secretion signal sequence is from a gram positive bacteria. In other aspects, the signal sequence can be from a gram negative bacteria (e.g., *E. coli*). For example, the signal sequence can be from murein lipoprotein (Lpp). In certain aspects, the secretion signal sequence comprises a sequence at least 90%, 91%, 92%, 93%, 94%, 95%, 96%, 97%, 98%, 99% or 100% identical to SEQ ID NO: 2. Further aspects, the signal sequence can be a signal sequence from an autotransporter polypeptide of a gram negative bacteria. For example, the signal sequence can be from AIDA-I, EstA, MisL, Hbp, Ag43, BrkA, OmpA, OmpC, OmpX, LamB, FhuA, Pfal, EspP, IgAP, Pet or Yfal (see, e.g., Nicolay et al., 2015 and van Bloois et al., 2011, each incorporated herein by reference).

b. Membrane Anchor Sequence

Certain aspect of the embodiments concern fusion polypeptides that comprise a bacterial membrane anchor sequence. For example, the membrane anchor sequence can be composed of all or part of an integral membrane protein from a gram negative or gram positive bacteria. In further aspects, the membrane anchor sequence can be a non-integral membrane polypeptide, such as a lipoprotein or a component of a bacterial surface appendage, caspule or cell wall. In particular aspects, the bacterial membrane anchor sequence can be an outer membrane anchor sequence. In some aspects, the sequence can be a beta-barrel domain from an autotransporter polypeptide of a gram negative bacteria. For example, the membrane anchor sequence can comprise a membrane anchor domain from AIDA-I, EstA, MisL, Hbp, Ag43, BrkA, OmpA, OmpC, OmpX, LamB, FhuA, Pfal, EspP, IgAP, Pet, Yfal or MraY (see, e.g., Nicolay et al., 2015 and van Bloois et al., 2011, each incorporated herein by reference). In further aspects, the bacterial membrane anchor sequence comprises the membrane anchor sequence from OmpA. In some aspects, the bacterial membrane anchor sequence comprises a sequence at least 90%, 91%, 92%, 93%, 94%, 95%, 96%, 97%, 98%, 99% or 100% identical to SEQ ID NO: 1.

c. Linker Sequence

It will be understood that in certain cases, a fusion polypeptide may comprise additional amino acids positioned between the candidate polypeptide sequence and the membrane anchor sequence. In general these sequences are interchangeably termed "linker sequences" or "linker regions." One of skill in the art will recognize that linker regions may be one or more amino acids in length and often comprise one or more glycine residue(s) which confer flexibility to the linker. A variety of linkers can be used as part of fusion polypeptide of the embodiments. In preferred aspects, the optional linker sequence is positioned between the membrane anchor sequence and the candidate polypeptide sequence. In certain aspects the linker sequence comprises at least or about 1, 2, 3, 4, 5, 6, 7, 8, 9, 10, 11, 12, 13, 14, 15, 16, 17, 18, 19 or 20 amino acids. In still further aspects the linker comprises between about 10 and 200, 10 and 100, 20 and 100, 40 and 100 or 50 and 90 amino acids.

In certain aspects, the linker sequence may comprise two, three, four or more Gly positions or a poly Gly sequence having two or more consecutive Gly positions. In particular aspects, the linker sequence comprises a sequence at least 90%, 91%, 92%, 93%, 94%, 95%, 96%, 97%, 98%, 99% or 100% identical to SEQ ID NO: 3; SEQ ID NO: 4 (GST-SGSGKPGSGEGSTKG); SEQ ID NO: 5 (EAAAK); or SEQ ID NO: 6 (GGGGS). In still further aspects, a linker comprises two, three or more repeats of a sequence at least 90%, 91%, 92%, 93%, 94%, 95%, 96%, 97%, 98%, 99% or 100% identical to SEQ ID NO: 3; SEQ ID NO: 4; SEQ ID NO: 5; or SEQ ID NO: 6. In some cases, such linker sequences can be repeated 1, 2, 3, 4, 5, 6, or more times or combined with one or more different linkers to form an array of linker sequences. For example, the linker sequence can comprise two consecutive repeats of a sequence according to SEQ ID NO: 4.

In still further aspects, the linker sequence can comprise all or part of a bacterial membrane polypeptide (e.g., a gram negative outer membrane polypeptide). In some aspects, the linker is a portion of sequence from a *Neisseria* polypeptide. For example, the linker can comprise 10, 15, 20, 25, 30, 35, 40 or more consecutive amino acid from any one of SEQ ID NOs:7-26. In still further aspects, the linker comprises a sequence at least 90%, 91%, 92%, 93%, 94%, 95%, 96%, 97%, 98%, 99% or 100% identical to any one of SEQ ID NOs:7-26.

In further aspects, a linker sequence may comprise a protease cleavage site, such as the cleavage site recognized by an extracellular protease. In still further aspects, a protease cleavage site can be a site that is by a recombinant protease. In certain aspects, a linker can comprise cleavage site that is cleaved by urokinase, plasmin, thrombin, Factor IXa, Factor Xa, or a metalloproteinase, such as collagenase, gelatinase, or stromelysin.

d. Candidate Polypeptide

In certain aspects, the candidate polypeptide sequence(s) may be from about 10, 15, 20, 25, 30, 35, 40, 45, 50, 60, 70, 80, 90, 100, 125, 150, 175, 200 to about 300 amino acids in length. In some aspects, the candidate polypeptide sequences can be a sequence based on a known polypeptide (e.g., a polypeptide having a known antibiotic activity) that has been randomly or selectively mutated. In further aspects, candidate polypeptide sequences can be a randomized group of sequences.

III. Host Cells

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular aspects, a host cell is a Gram negative bacterial cell. In still further aspects, the host cell is a gram positive bacterial cell. For example, in some aspects, the host cell can a human bacterial pathogen such as a *Bacillus anthracis, Bordetella pertussis, Borrelia burgdorferi, Brucella abortus, Brucella canis, Brucella melitensis, Brucella suis, Burkholderia cepacia, Burkholderia pseudomallei, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli* (e.g., Enteropathogenic *E. coli*, Enterotoxigenic *E. coli* or *E. coli* O157:H7), *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitides, Pseudomonas aeruginosa, Rickettsia rickettsia, Salmonella typhi, Salmonella typhimurium, Shigella sonnei, Staphylococcus aureusa, Staphylococcus epidermidis, Staphylococcus saprophyticus, Streptococcus agalactiae, Streptococcus pneumonia, Streptococcus pyogenes, Treponema pallidum, Vibrio cholera,* or *Yersinia pestis* bacterial cell. In still further aspects, the host cell can be laboratory strain of bacteria that is used for screening antibiotic activity. In still further aspects, the host cell can be a bacterial cell having resistance to an antibiotic.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Peptide-Screening Platform

The inventors' platform creates microenvironments for individual bacteria and peptide sequences to interact under physiologically relevant conditions, within a mixed bacterial population. Lytic events are measured using next-generation sequencing, allowing rapid and batch screening of millions of peptides for antimicrobial activity in a single tube.

The inventors' peptide-screening platform (exemplified in FIG. 1) is engineered from four components: (1) the murein lipoprotein (Lpp) signal sequence that directs proteins for export from the cytoplasm and is subsequently cleaved, (2) five loops of the gram-negative outer membrane protein OmpA that anchors our system to the cell surface, (3) a flexible tether (optional) that allows spatial freedom past the outer membrane, and (4) a C-terminal peptide. The bacterial transport machinery utilized by this system ensures that the construct does not interact with cellular components until it is localized to the surface, alleviating the burden of intracellular toxicity. The inventors have engineered the unstructured, low-complexity-region protein from the *Neisseria* genus into this system to act as a flexible tether connecting the membrane anchoring OmpA component to the C-terminal peptide. Two low-complexity-region proteins fused together (2× tether) produces a flexible tether that extends up to 20 nm. This length allows C-terminal peptides to interact with the cell surface and also to penetrate the cell surface and interact with periplasmic components. Through these interactions, C-terminal peptides exhibiting antimicrobial activity lyse the bacteria expressing them thereby eliminating themselves from the population.

Example 2—Screening Experiments Using the Platform

Figure 2A:
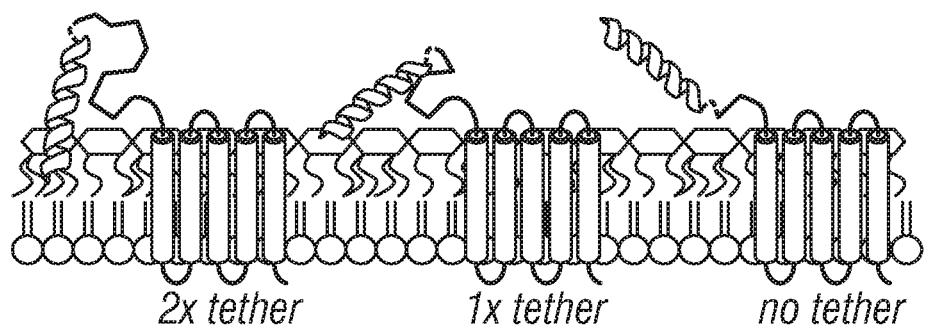
Figure 2B:
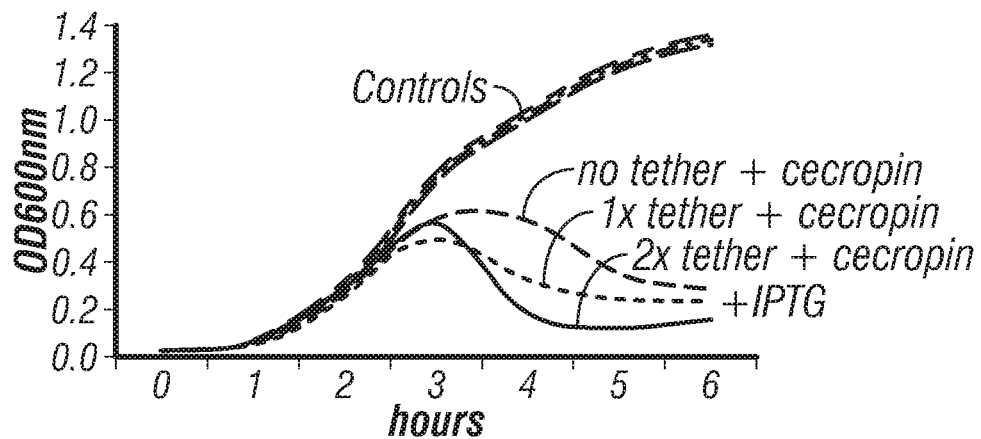
Figure 2D:
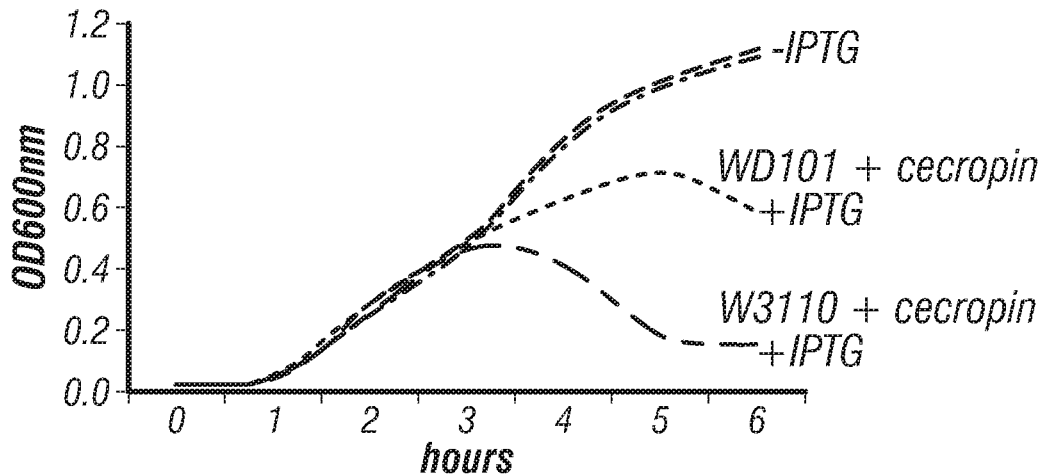

For a proof of concept experiment, the inventors used the antimicrobial peptide cecropin P1 that effectively lyses many gram-negative bacteria through disruption of the outer membrane. The inventors attached cecropin P1 to the Lpp-OmpA surface display system alone and by one (1×) or two (2×) low-complexity-region protein tethers (FIG. 2A). A tandem influenza hemagglutinin (2×HA) peptide was used as a control peptide as it does not have antimicrobial peptide activity. When these constructs are induced in wild type *E. coli* strain W3110 by addition of IPTG, the Lpp signal sequence directs secretion, and the OmpA-tether-peptide fusions translocate to the cell surface where the peptides exert their action. In the absence of IPTG, all cultures grow similarly (FIG. 2B, Controls). When IPTG is added, cultures expressing cecropin P1 constructs begin to lyse as measured by a decrease in culture optical density (FIG. 2B). The rate and amount of cell lysis is dependent upon the tether. Using two (2×) tandem low-complexity-region proteins to tether cecropin P1 to the surface gives the most efficient lysis. Cultures expressing control 2×HA constructs are unaffected by IPTG induction (FIG. 2B, Controls). Increasing concentrations of IPTG lead to increased cell lysis (FIG. 2C). Dermaseptin is another antimicrobial peptide with a very different sequence than cecropin P1[37]. Swapping dermaseptin for cecropin P1 shows the same impact on cell growth following induction indicating that our system is amenable to a variety of peptide sequences (FIG. 2C). The isogenic *E. coli* strain WD101 carries a mutation in its lipopolysaccharide layer in the outer membrane that makes it resistant to antimicrobial peptides including cecropin P1[38]. When the inventors' cecropin P1 encoding surface display system is expressed in this resistant strain, less cell lysis compared to the parental strain W3110 was observed, consistent with increased resistance of WD101 to cecropin P1 (FIG. 2D). This result supports the ability of the inventors' platform to maintain the native activity and biologically relevant interactions of antimicrobial peptides at the cell surface.

Example 3—Platform Characterization

Figure 2E:
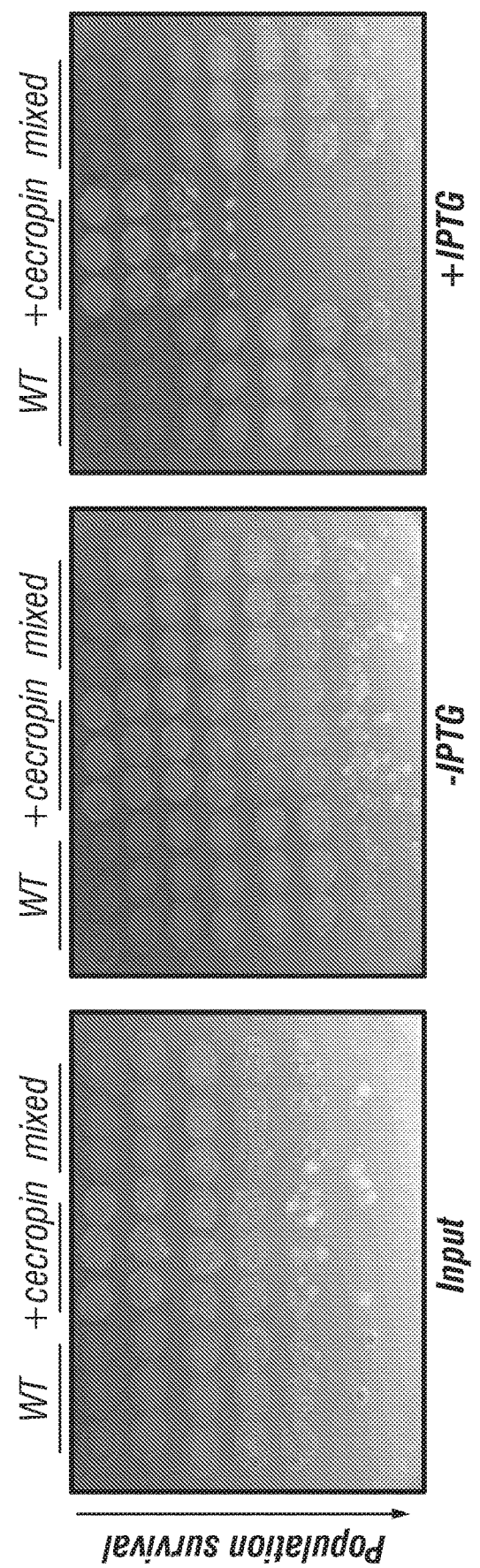

An essential innovation of the platform was the design of a tether that allows for movement of the C-terminal peptide, but also restricts it from interacting with neighboring bacteria. As shown in FIG. 2E, when a population of 2× tether+cecropin P1 expressing *E. coli* (white) and control *E. coli* cells carrying an empty vector (blue) are co-cultured in equal ratio, induction of cecropin P1 by IPTG only affects the viability of bacteria expressing cecropin P1, eliminating them from the pool and leaving the control bacteria intact. In 3 hours, a 2-3-log difference in recoverable colony forming units between cecropin P1 expressing and control bacteria was observed (FIG. 2E). Agreeing with this result, quantitative PCR analysis of plasmids isolated from this co-culture after IPTG induction shows that the ratio of cecropin P1 encoding plasmid to empty vector decreases approximately ~50-fold in 3 hours (FIG. 2F).

Figure 3:
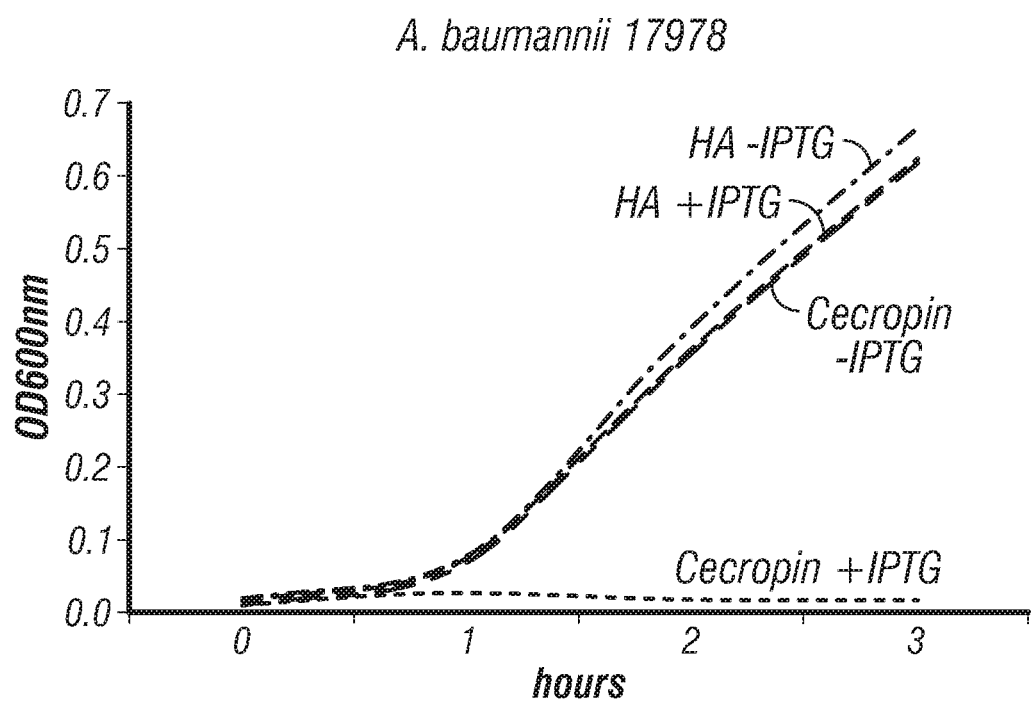
FIG. 3: Surface expression of 2× tether+cecropin P1 or HA in *A. baumannii*. Addition of IPTG leads to rapid lysis of cecropin P1 containing *A. baumannii*.

The platform uses a plasmid with a broad host range origin of replication offering flexibility to identify antimicrobial peptides in many gram-negative bacteria. For example, *A. baumannii* is a gram-negative, hospital-associated pathogen that quickly acquires antibiotic resistance. Without any modifications, the methods described herein can move the a screened-cecropin P1 surface display construct into *A. baumannii* and show that it functions in a similar manor to *E. coli* (FIG. 3). The selective marker on this plasmid can be changed to allow its use in bacteria with different antibiotic resistant profiles.

A significant advancement of this platform is using next-generation sequencing to quantify the antimicrobial activity of individual peptides as part of a massive pool. This increases throughput while greatly reducing screening costs. The inventors' platform uses simple subtractive analysis of output from input library pools to determine peptide sequences that cause cell lysis and eliminate themselves from the input pool. One lane of a standard HiSeq Illumina sequencer generates 200 million sequencing reads. Allowing for 20-fold starting coverage of each peptide in our library, a 5 mL culture and one Illumina sequence lane would allow for the screening of 20 million peptides for approximately $1,000 US dollars after library construction.

Example 4—Platform Workflow Experiment

Figure 5A:
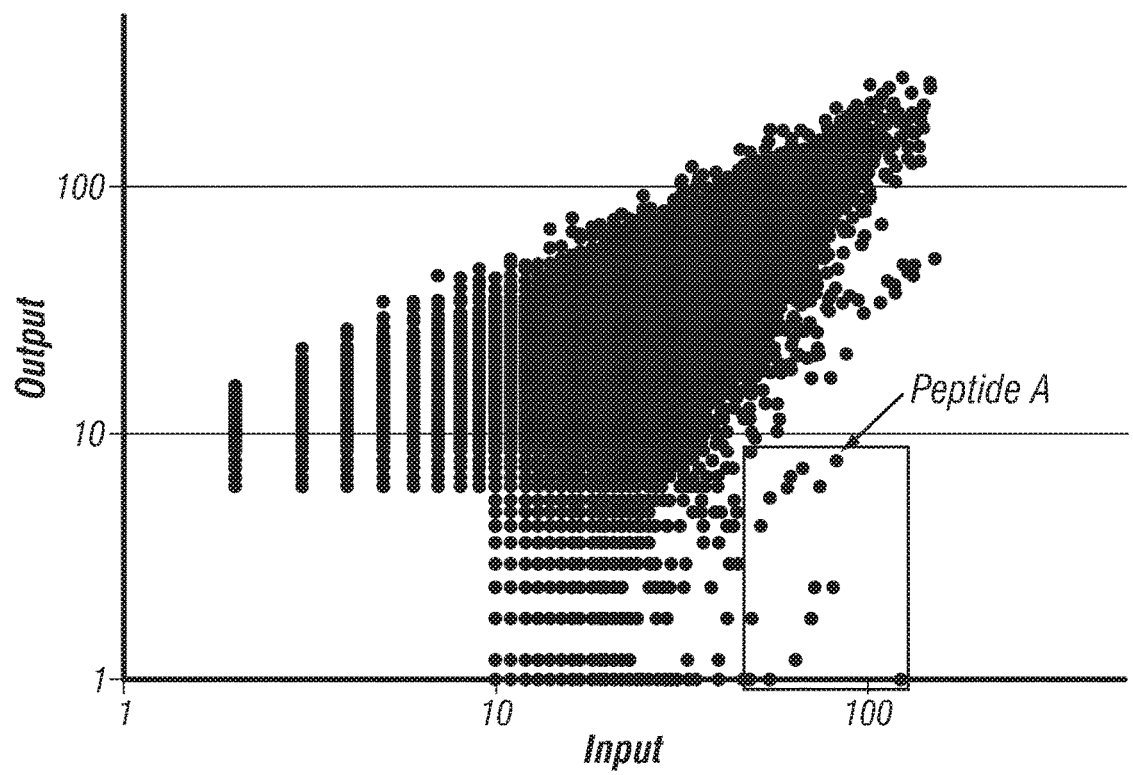
FIGS. 5A-B: (A) Abundance of sequencing reads from the input library is plotted against abundance of sequencing reads from a representative output sample. The red box encloses peptides that are 15-125 fold depleted in the output samples. (B) Peptide A, shown in panel 5A, was re-cloned into our surface expression system and grown in wild type W3110 *E. coli* and the isogenic antimicrobial resistant *E. coli* strain WD101. IPTG induction of Peptide A led to cell lysis of both strains. Lysis by cecropin P1 is shown as a control.
Figure 5B:
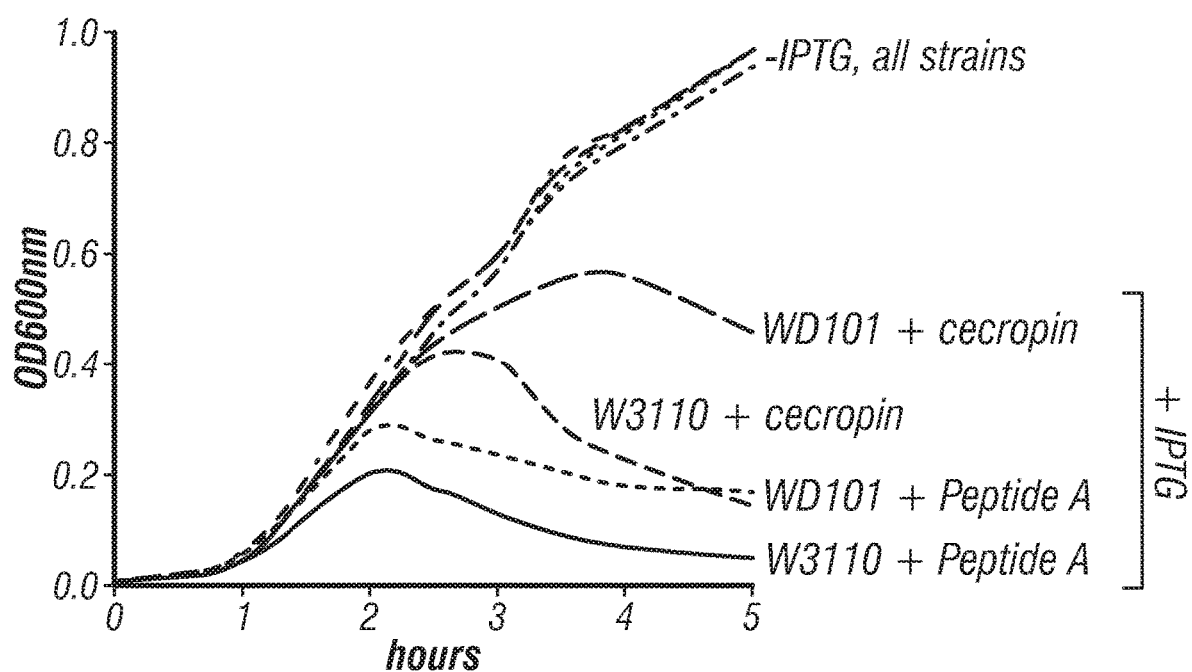

The workflow for the platform is shown in FIG. 4. Using this workflow, the inventors performed a proof of principle experiment, to validate the use of the platform to identify potent antimicrobial peptides. A small 90,000-clone peptide library was generated by cloning a random 60 nucleotide peptide coding DNA duplex into the inventors' surface expression system. The library was transformed into the antimicrobial peptide resistant *E. coli* strain WD101 (FIG. 2D) and grown in biological duplicates in the presence of 0.1 mM IPTG for 3 hours. Then plasmids were isolated from intact bacteria. Approximately 2 million sequencing reads for input and output samples were acquired, giving ~20 fold coverage of each input peptide sequence. The output samples were computationally translated and compared to the input library to identify peptides that were depleted after the 3-hour incubation. FIG. 5A shows the abundance of each peptide in the input library plotted against its abundance in a representative output library. The input library was spiked with strain WD101 carrying the inventors' cecropin P1 construct as a control. Importantly, the output/input ratio of cecropin P1 did not change, agreeing with the cecropin P1 resistant phenotype of WD101. The output/input ratio for the majority of peptides in the library did not change, however 15 peptides that decreased 15-125 fold after IPTG induction in both biological replicates were identified (FIG. 5A, red box). BLAST analysis demonstrated that these peptides do not have sequence similarity to any known antimicrobial peptide. These 15 peptides represent novel candidate peptides that may be effective against *E. coli* WD101, which is resistant to all currently known antimicrobial peptides including colistin, the antibiotic of last resort. Induction of the first peptide the inventors have re-cloned, Peptide A (FIG. 5A), in wild type W3110 and resistant WD101 *E. coli* strains led to more effective cell lysis then cecropin P1 (FIG. 5B). As with cecropin P1, Peptide A has a stronger effect on the wild type *E. coli* W3110 than the resistant strain WD101. This suggests that Peptide A acts at the surface like cecropin P1, but is much more effective.

Figure 7A:
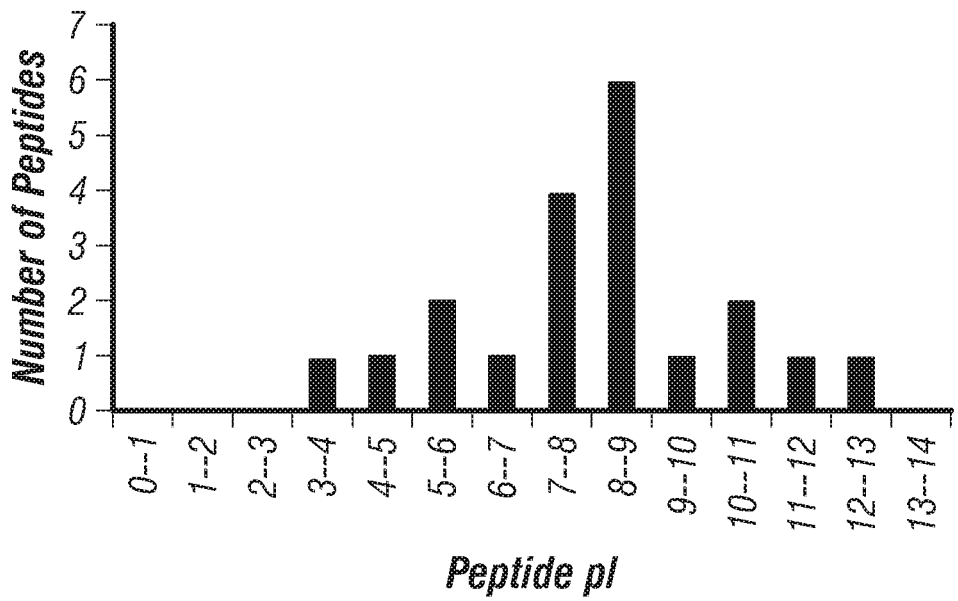
FIGS. 7A-B: Top antimicrobial peptides identified in inventors' screen plotted by abundance vs (A) pI at pH 7.0 and (B) charge.
Figure 7B:
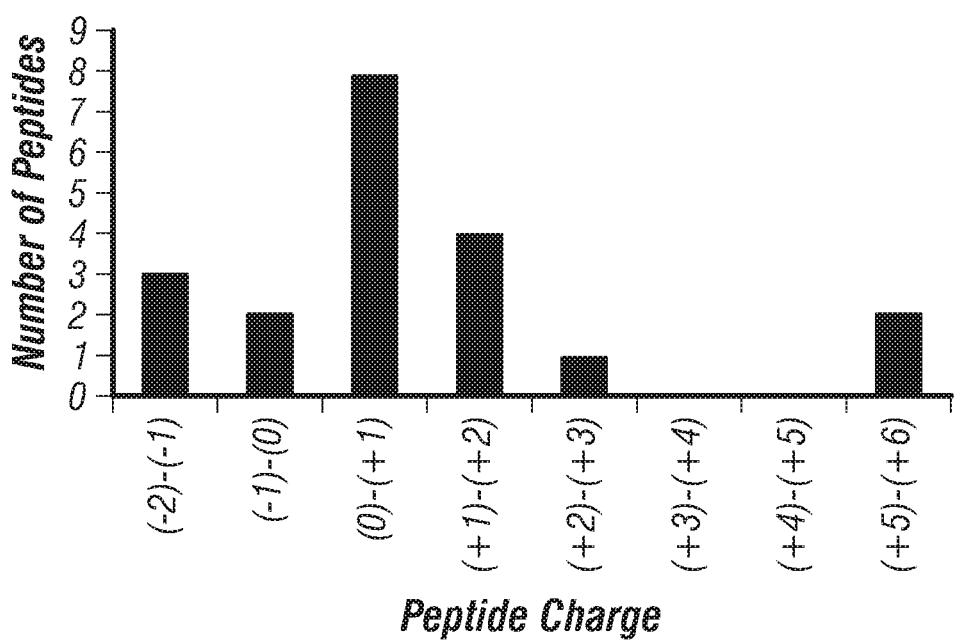

The majority of antimicrobial peptides under investigation are cationic[9,25-27]. The positive charge is thought to interact with the negative charge found on surface of several bacteria. The inventors binned Peptide A and an additional 14 potential antimicrobial peptides identified in this screen (FIG. 5A, red box) by charge and isoelectric point (FIGS. 7A-B). Rather than a bias towards strong cationic character, the average peptide charge was found to be nearly neutral at +1, with several potential antimicrobial peptides exhibiting a net negative charge and corresponding acidic pI at pH 7.0.

The inventors chemically synthesized Peptide A and tested its antimicrobial activity against *E. coli* in vitro. *E. coli* was incubated with increasing concentrations of Peptide A for 1 hour, then serially diluted in 10-fold increments and plated to determine the remaining number of viable bacteria. FIG. 6 demonstrates that Peptide A effectively kills an antibiotic resistant strain of bacteria. The platform described herein is readily amenable to adaptations. Developments in non-natural amino acids and alternative codon usage offer potential to expand the inventors' peptide library diversity. Combining this system with periplasmic and outer membrane modifying enzymes offers the possibility of creating peptide libraries with lipid and/or sugar modifications to enhance their activity. Importantly, the use of subtractive sequencing analysis also makes this system amenable to selection in cell culture and in animal models to further approximate host conditions.

Example 5—In Vivo Screening Experiment

Figure 8:
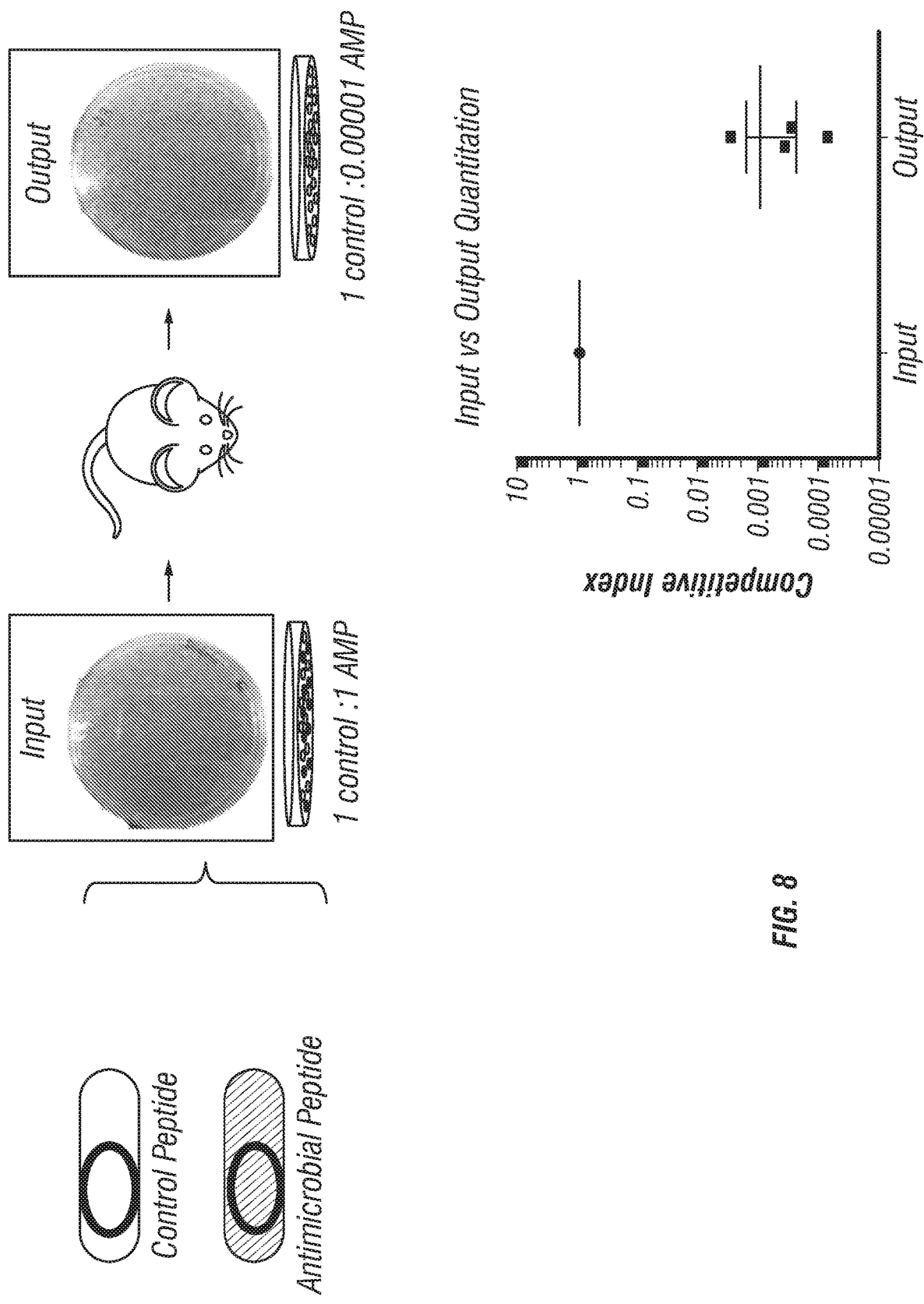
FIG. 8: In vivo peptide screening. Expression of the peptide surface display system is placed under control of a *V. cholerae* virulence promoter. White *V. cholerae* expresses a non-lethal control peptide. Blue *V. cholerae* expresses a lethal AMP. Neither peptide is expressed in vitro. The input inoculum contains both white and blue *V. cholerae* at a 1:1 ratio. This input mixture is inoculated in a mouse. In the mouse, the virulence promoter is activated and drives expression of the peptide surface display system. There is no effect on white *V. cholerae*. Blue *V. cholerae* expressing the lethal AMP is killed inside the mouse resulting in greatly diminished presence in the output bacteria quantitation (see graph).

The previously described screening platform used an IPTG inducible tac promoter to drive expression of the peptide surface display system. By changing the inducible promoter used the signal that activates peptide surface-display expression can be altered. In this case, the tac promoter is replaced with a promoter that is activated in vivo at the site of infection. For example, studies were untaken using the *V. cholerae* virulence promoter to drive expression of the peptide surface display system (see FIG. 8). White *V. cholerae* expresses a non-lethal control peptide whereas blue *V. cholerae* expresses a lethal AMP. Neither peptide is expressed in vitro when the strains are grown under normal lab conditions (since the virulence promoter is inactive). These two strains are mixed together in the input inoculum at a 1:1 ratio. This input mixture is inoculated in a mouse. In the mouse, the virulence promoter is activated and drives expression of the peptide surface display system. There is no effect on white *V. cholerae* expressing the control peptide. Blue *V. cholerae* expressing the lethal AMP are killed inside the mouse resulting in greatly diminished presence in the output bacteria quantitation. By constructing large peptide libraries and placing their surface expression under the control of in vivo activated promoters we can screen for antimicrobial peptides that are active at the site of infection.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel et al., In: Current Protocols in Molecular Biology, John, Wiley & Sons, Inc, N Y, 1994.

Bahar, A. A. & Ren, D., Antimicrobial Peptides; Pharmaceuticals 6, 1543-1575, 2013.

Bergen, P. J. et al., 'Old' antibiotics for emerging multidrug-resistant bacteria; [Miscellaneous Article]. Curr. Opin. Infect. Dis. Dec. 2012 25, 626-633, 2012.

Carbonelli et al., FEMS Microbiol Lett., 177:75-82. 1999.

CDC. *Antibiotic Resistance Threats in the United States*. (U.S. Department of Health and Human Services, 2013). at <http://www.cdc.gov/drugresistance/threat-report, 2013.

Cherkasov, A. et al., Use of Artificial Intelligence in the Design of Small Peptide Antibiotics Effective against a Broad Spectrum of Highly Antibiotic-Resistant Superbugs. ACS; Chem. Biol. 4, 65-74, 2009.

Clatworthy, A. E. et al., Targeting virulence: a new paradigm for antimicrobial therapy; Nat. Chem. Biol. 3, 541-548, 2007.

Cocea, Biotechniques, 23(5):814-816, 1997.

Deslouches, B. et al., De Novo Generation of Cationic Antimicrobial Peptides: Influence of Length and Tryptophan Substitution on Antimicrobial Activity; Antimicrob. Agents Chemother. 49, 316-322, 2005.

Fagerlund, A., Myrset, A. H. & Kulseth, M. A. in Therapeutic Peptides (ed. Nixon, A. E.) 19-33 (Humana Press). at http://link.springer.com/protocol/10.1007/978-1-62703-673-3_2, 2014.

Fischbach, M. A. & Walsh, C. T, Antibiotics for emerging pathogens; Science 325, 1089-1093, 2009.

Fjell, C. D., Designing antimicrobial peptides: form follows function; Nat. Rev. Drug Discov. 11, 37-51, 2012.

Fox, J. L., et al., Antimicrobial peptides stage a comeback; Nat. Biotechnol. 31, 379-382, 2013.

Fu, J. et al., Full-length RecE enhances linear-linear homologous recombination and facilitates direct cloning for bioprospecting; Nat. Biotechnol. 30, 440-446, 2012.

Gould, I. M. & Bal, A. M., New antibiotic agents in the pipeline and how they can help overcome microbial resistance; Virulence 4, 185-191, 2013.

Guilhelmelli, F. et al., Antibiotic development challenges: the various mechanisms of action of antimicrobial peptides and of bacterial resistance; Antimicrob. Resist. Chemother. 4, 353, 2013.

Guralp, S. A. et al., From Design to Screening: A New Antimicrobial Peptide Discovery Pipeline; PLoS ONE 8, e59305, 2013.

Hartigan, J., Compound Profiling: size impact on primary screening libraries. Spring 10; Drug Discovery World, http://www.ddw-online.com/p-92823, 2010.

Hilpert, K., et al., Peptide arrays on cellulose support: SPOT synthesis, a time and cost efficient method for synthesis of large numbers of peptides in a parallel and addressable fashion; Nat. Protoc. 2, 1333-1349, 2007.

Klevens, R. M. et al. Estimating health care-associated infections and deaths in U.S. hospitals, 2002. Public Health Rep. Wash. D.C. 1974 122, 160-166, 2007.

Lee, J. Y. et al., Antibacterial peptides from pig intestine: isolation of a mammalian cecropin; Proc. Natl. Acad. Sci. 86, 9159-9162, 1989.

Levenson et al., 1998.

Liew et al., Microbiol., 157:666-676, 2011.

Liu, Z. et al., Length Effects in Antimicrobial Peptides of the (RW)n Series; Antimicrob. Agents Chemother. 51, 597-603, 2007.

Maniatis, et al., Molecular Cloning, A Laboratory Manual, Cold Spring Harbor Press, Cold Spring Harbor, N.Y., 1988.

Man, A. K. et al., Antibacterial peptides for therapeutic use: obstacles and realistic outlook; Curr. Opin. Pharmacol. 6, 468-472, 2006.

Nicolay et al., Crit. Rev. Microbiol., 41(1):109-123, 2015

O'Neil, J. Antimicrobial Resistance: Tackling a crisis for the health and wealth of nations. (United Kingdom, 2014).

Otvos, L., Peptide-Based Drug Design (ed. Otvos, L.) 1-8 (Humana Press) at http://link.springer.com/protocol/10.1007/978-1-59745-419-3_1, 2008.

Peschel, A. & Sahl, H.-G, The co-evolution of host cationic antimicrobial peptides and microbial resistance; Nat. Rev. Microbiol. 4, 529-536, 2006.

Rathinakumar, R. & Wimley, W. C., High-throughput discovery of broad-spectrum peptide antibiotics; FASEB J. 24, 3232-3238, 2010.

Sivertsen, A. et al., Synthetic cationic antimicrobial peptides bind with their hydrophobic parts to drug site II of human serum albumin; BMC Struct. Biol. 14, 4, 2014.

Upton, M., Cotter, P. & Tagg, J., Antimicrobial Peptides as Therapeutic Agents; Int. J. Microbiol. 2012, e326503, 2012.

Van Bloois et al., Applied Microbiol. 29(2):79-86, 2011.

Wiesner, J. & Vilcinskas, A., Antimicrobial peptides: The ancient arm of the human immune system; Virulence 1, 440-464, 2010.

---

What is claimed is:

1. A method for identifying a polypeptide having antibiotic activity comprising:
   (a) obtaining a bacterial cell, said cell comprising a nucleic acid construct encoding a fusion protein under the control of an inducible promoter, said fusion protein comprising:
      (i) a secretion signal sequence;
      (ii) a candidate polypeptide sequence;
      (iii) a linker comprising a sequence at least 90% identical to SEQ ID NO: 3, wherein said linker does not comprise a protease cleavage site; and
      (iv) a bacterial membrane anchor sequence;
   (b) culturing the bacterial cell in vitro to induce expression of the fusion protein in the bacterial cell, wherein said fusion protein is anchored to the surface membrane of said bacterial cell; and
   (c) identifying whether the candidate polypeptide sequence has antibiotic activity against the bacterial cell, the identifying comprising identifying whether the bacterial cell undergoes lysis after the inducing step.

2. The method of claim 1, further comprising performing sequencing of the nucleic acid constructs before said inducing step and performing sequencing from the intact cell after said inducing step to identify the candidate polypeptide sequences having antibiotic activity.

3. The method of claim 1, wherein the encoded fusion protein comprises, from N- to C-terminus: (i) a secretion signal sequence; (ii) a candidate polypeptide sequence; (iii) a linker sequence; and (iv) a bacterial membrane anchor sequence.

4. The method of claim 1, wherein the encoded fusion protein comprises, from N- to C-terminus: (i) a secretion signal sequence; (iv) a bacterial membrane anchor sequence; (iii) a linker sequence; and (ii) a candidate polypeptide sequence.

5. The method of claim 1, wherein obtaining the bacterial cell comprises transforming a bacterial cell with said nucleic acid construct, wherein the nucleic acid construct encodes at least one candidate polypeptide sequence.

6. The method of claim 1, wherein the bacterial membrane anchor sequence comprises a sequence at least 90% identical to SEQ ID NO: 1 (NPYVGFEMGYDWLGRMPYKGS-VENGAYKAQGVQLTAKLGYPITDDLDIYTRLGGMV WRADTKSNVYGKNHDTGVSPVFAGGVEYAITPEI-ATRLEYQWTNNIGDAHTIGTRPDN).

7. A recombinant bacterial cell, comprising a heterologous nucleic acid construct encoding a fusion protein under the control of an inducible promoter, said fusion protein comprising:
   (i) a secretion signal sequence;
   (ii) a candidate polypeptide sequence;
   (iii) a linker sequence comprising a sequence at least 90% identical to SEQ ID NO: 3, wherein said linker does not comprise a protease cleavage site; and
   (iv) a bacterial membrane anchor sequence,
wherein said fusion protein in anchored to the surface membrane of said recombinant bacterial cell.

8. The recombinant bacterial cell of claim 7, wherein the encoded fusion protein comprises, from N- to C-terminus: (i) a secretion signal sequence; (ii) a candidate polypeptide sequence; (iii) a linker sequence; and (iv) a bacterial membrane anchor sequence.

9. The recombinant bacterial cell of claim 7, wherein the encoded fusion protein comprises, from N- to C-terminus: (i) a secretion signal sequence; (iv) a bacterial membrane anchor sequence; (iii) a linker sequence; and (ii) a candidate polypeptide sequence.

10. The recombinant bacterial cell of claim 7, wherein the linker sequence comprises at least two repeats of a sequence at least 90% identical to SEQ ID NO: 3 (SQEPAAPAAEAT-PAAEAPASEAPAAEAAPADAAEAPAAGI).

* * * * *

SEQUENCE LISTING

<160> NUMBER OF SEQ ID NOS: 26

<210> SEQ ID NO 1
<211> LENGTH: 114
<212> TYPE: PRT
<213> ORGANISM: Escherichia coli

<400> SEQUENCE: 1

```
Asn Pro Tyr Val Gly Phe Glu Met Gly Tyr Asp Trp Leu Gly Arg Met
1               5                   10                  15

Pro Tyr Lys Gly Ser Val Glu Asn Gly Ala Tyr Lys Ala Gln Gly Val
            20                  25                  30

Gln Leu Thr Ala Lys Leu Gly Tyr Pro Ile Thr Asp Asp Leu Asp Ile
        35                  40                  45

Tyr Thr Arg Leu Gly Gly Met Val Trp Arg Ala Asp Thr Lys Ser Asn
    50                  55                  60

Val Tyr Gly Lys Asn His Asp Thr Gly Val Ser Pro Val Phe Ala Gly
65                  70                  75                  80

Gly Val Glu Tyr Ala Ile Thr Pro Glu Ile Ala Thr Arg Leu Glu Tyr
                85                  90                  95
```

```
Gln Trp Thr Asn Asn Ile Gly Asp Ala His Thr Ile Gly Thr Arg Pro
            100                 105                 110
Asp Asn

<210> SEQ ID NO 2
<211> LENGTH: 29
<212> TYPE: PRT
<213> ORGANISM: Escherichia coli

<400> SEQUENCE: 2

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln
            20                  25

<210> SEQ ID NO 3
<211> LENGTH: 40
<212> TYPE: PRT
<213> ORGANISM: Neisseria meningitidis

<400> SEQUENCE: 3

Ser Gln Glu Pro Ala Ala Pro Ala Ala Glu Ala Thr Pro Ala Ala Glu
1               5                   10                  15

Ala Pro Ala Ser Glu Ala Pro Ala Ala Glu Ala Ala Pro Ala Asp Ala
            20                  25                  30

Ala Glu Ala Pro Ala Ala Gly Ile
            35                  40

<210> SEQ ID NO 4
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 4

Gly Ser Thr Ser Gly Ser Gly Lys Pro Gly Ser Gly Glu Gly Ser Thr
1               5                   10                  15

Lys Gly

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 5

Glu Ala Ala Ala Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 6

Gly Gly Gly Gly Ser
1               5

<210> SEQ ID NO 7
```

<211> LENGTH: 201
<212> TYPE: PRT
<213> ORGANISM: Neisseria meningitidis

<400> SEQUENCE: 7

```
Met His Phe Asp Phe Cys Lys Thr Glu Tyr Tyr Phe Ile Asp Trp Arg
1               5                   10                  15
Phe Val Met Lys Ala Tyr Leu Ala Leu Ile Ser Ala Ala Val Ile Gly
                20                  25                  30
Leu Ala Ala Cys Ser Gln Glu Pro Ala Ala Pro Ala Glu Ala Thr
                35                  40                  45
Pro Ala Ala Glu Ala Pro Ala Ser Glu Ala Pro Ala Glu Ala Ala
    50                  55                  60
Pro Ala Asp Ala Ala Glu Ala Pro Ala Ala Gly Asn Cys Ala Ala Thr
65                  70                  75                  80
Val Glu Ser Asn Asp Asn Met Gln Phe Asn Thr Lys Asp Ile Gln Val
                85                  90                  95
Ser Lys Ala Cys Lys Glu Phe Thr Ile Thr Leu Lys His Thr Gly Thr
                100                 105                 110
Gln Pro Lys Ala Ser Met Gly His Asn Leu Val Ile Ala Lys Ala Glu
            115                 120                 125
Asp Met Asp Gly Val Phe Lys Asp Gly Val Gly Ala Ala Asp Thr Asp
        130                 135                 140
Tyr Val Lys Pro Asp Asp Ala Arg Val Val Ala His Thr Lys Leu Ile
145                 150                 155                 160
Gly Gly Gly Glu Glu Ala Ser Leu Thr Leu Asp Pro Lys Leu Ala
                165                 170                 175
Asp Gly Glu Tyr Lys Phe Ala Cys Thr Phe Pro Gly His Gly Ala Leu
            180                 185                 190
Met Asn Gly Lys Val Thr Leu Val Asp
            195                 200
```

<210> SEQ ID NO 8
<211> LENGTH: 201
<212> TYPE: PRT
<213> ORGANISM: Neisseria meningitidis

<400> SEQUENCE: 8

```
Met His Phe Asp Phe Cys Lys Thr Glu Tyr Tyr Phe Ile Asp Trp Arg
1               5                   10                  15
Phe Thr Met Lys Ala Tyr Leu Ala Leu Ile Ser Ala Ala Val Ile Gly
                20                  25                  30
Leu Ala Ala Cys Ser Gln Glu Pro Ala Ala Pro Ala Glu Ala Thr
                35                  40                  45
Pro Ala Ala Glu Ala Pro Ala Ser Glu Ala Pro Ala Ala Glu Ala Ala
    50                  55                  60
Pro Ala Asp Ala Ala Glu Ala Pro Ala Ala Gly Asn Cys Ala Ala Thr
65                  70                  75                  80
Val Glu Ser Asn Asp Asn Met Gln Phe Asn Thr Lys Asp Ile Gln Val
                85                  90                  95
Ser Lys Ala Cys Lys Glu Phe Thr Ile Thr Leu Lys His Thr Gly Thr
                100                 105                 110
Gln Pro Lys Ala Ser Met Gly His Asn Leu Val Ile Ala Lys Ala Glu
            115                 120                 125
Asp Met Asp Gly Val Phe Lys Asp Gly Val Gly Ala Ala Asp Thr Asp
        130                 135                 140
```

```
Tyr Val Lys Pro Asp Asp Ala Arg Val Val Ala His Thr Lys Leu Ile
145                 150                 155                 160

Gly Gly Gly Glu Glu Ser Ser Leu Thr Leu Asp Pro Ala Lys Leu Ala
                165                 170                 175

Asp Gly Asp Tyr Lys Phe Ala Cys Thr Phe Pro Gly His Gly Ala Leu
            180                 185                 190

Met Asn Gly Lys Val Thr Leu Val Asp
        195                 200

<210> SEQ ID NO 9
<211> LENGTH: 183
<212> TYPE: PRT
<213> ORGANISM: Neisseria polysaccharea

<400> SEQUENCE: 9

Met Lys Thr Tyr Leu Ala Leu Ile Ser Ala Val Ile Gly Leu Ala
1               5                   10                  15

Ala Cys Ser Gln Glu Pro Ala Ala Pro Ala Ala Glu Ala Thr Pro Ala
                20                  25                  30

Ala Glu Ala Pro Ala Ser Glu Ala Pro Ala Ala Glu Ala Ala Pro Ala
            35                  40                  45

Asp Ala Ala Glu Ala Pro Ala Ala Gly Asn Cys Ala Ala Thr Val Glu
        50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
                100                 105                 110

Asp Gly Val Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Ile Thr Leu Val Asp
            180

<210> SEQ ID NO 10
<211> LENGTH: 183
<212> TYPE: PRT
<213> ORGANISM: Neisseria meningitidis

<400> SEQUENCE: 10

Met Lys Ala Tyr Leu Ala Leu Ile Ser Ala Val Ile Gly Leu Ala
1               5                   10                  15

Ala Cys Ser Gln Glu Pro Ala Ala Pro Ala Glu Ala Thr Pro Ala
                20                  25                  30

Ala Glu Ala Pro Ala Ser Glu Ala Pro Ala Glu Ala Ala Pro Ala
            35                  40                  45

Asp Ala Ala Glu Ala Pro Ala Ala Gly Asn Cys Ala Ala Thr Val Glu
        50                  55                  60

Ser Asn Asp Asn Met Gln Phe Asn Thr Lys Asp Ile Gln Val Ser Lys
65                  70                  75                  80
```

```
Ala Cys Lys Glu Phe Thr Ile Thr Leu Lys His Thr Gly Thr Gln Pro
                85                  90                  95

Lys Thr Ser Met Gly His Asn Ile Val Ile Gly Lys Thr Glu Asp Met
            100                 105                 110

Asp Gly Ile Phe Lys Asp Gly Val Gly Ala Ala Gly Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Ile Thr Leu Val Asp
            180

<210> SEQ ID NO 11
<211> LENGTH: 183
<212> TYPE: PRT
<213> ORGANISM: Neisseria meningitidis

<400> SEQUENCE: 11

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Ile Gln Pro
                85                  90                  95

Lys Thr Ser Met Gly His Asn Ile Val Ile Gly Lys Thr Glu Asp Met
            100                 105                 110

Asp Gly Ile Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 12
<211> LENGTH: 183
<212> TYPE: PRT
<213> ORGANISM: Neisseria meningitidis

<400> SEQUENCE: 12

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30
```

```
Ala Glu Ala Pro Ala Ser Glu Ala Pro Ala Ala Glu Ala Pro Ala
        35                  40                  45

Asp Ala Ala Glu Ala Pro Ala Ala Gly Asn Cys Ala Ala Thr Val Glu
 50                  55                  60

Ser Asn Asp Asn Met Gln Phe Asn Thr Lys Asp Ile Gln Val Ser Lys
 65                  70                  75                  80

Ala Cys Lys Glu Phe Thr Ile Thr Leu Lys His Thr Gly Thr Gln Pro
                 85                  90                  95

Lys Thr Ser Met Gly His Asn Ile Val Ile Gly Lys Thr Glu Asp Met
            100                 105                 110

Asp Gly Ile Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Ile Thr Leu Val Asp
            180
```

```
<210> SEQ ID NO 13
<211> LENGTH: 183
<212> TYPE: PRT
<213> ORGANISM: Neisseria meningitidis

<400> SEQUENCE: 13
```

```
Met Lys Ala Tyr Leu Ala Leu Ile Ser Ala Ala Val Ile Gly Leu Ala
 1               5                  10                  15

Ala Cys Ser Gln Glu Pro Ala Ala Pro Ala Glu Ala Thr Pro Ala
                20                  25                  30

Ala Glu Ala Pro Ala Ser Glu Ala Pro Ala Ala Glu Ala Pro Ala
        35                  40                  45

Asp Ala Ala Glu Ala Pro Ala Ala Gly Asn Cys Ala Ala Thr Val Glu
 50                  55                  60

Ser Asn Asp Asn Met Gln Phe Asn Thr Lys Asp Ile Gln Val Ser Lys
 65                  70                  75                  80

Ala Cys Lys Glu Phe Thr Ile Thr Leu Lys His Thr Gly Thr Gln Pro
                 85                  90                  95

Lys Thr Ser Met Gly His Asn Ile Val Ile Gly Lys Thr Glu Asp Met
            100                 105                 110

Asp Gly Ile Phe Lys Asp Gly Val Gly Ala Ala Asp Thr Asp Tyr Val
            115                 120                 125

Lys Pro Asp Asp Ala Arg Val Val Ala His Thr Lys Leu Ile Gly Gly
        130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180
```

```
<210> SEQ ID NO 14
<211> LENGTH: 183
<212> TYPE: PRT
```

<213> ORGANISM: Neisseria meningitidis

<400> SEQUENCE: 14

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180

<210> SEQ ID NO 15
<211> LENGTH: 183
<212> TYPE: PRT
<213> ORGANISM: Neisseria meningitidis

<400> SEQUENCE: 15

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ala Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn

```
                    165                 170                 175

Gly Lys Val Thr Leu Val Asp
            180

<210> SEQ ID NO 16
<211> LENGTH: 183
<212> TYPE: PRT
<213> ORGANISM: Neisseria meningitidis

<400> SEQUENCE: 16

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp His Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 17
<211> LENGTH: 183
<212> TYPE: PRT
<213> ORGANISM: Neisseria meningitidis

<400> SEQUENCE: 17

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
```

```
            115                 120                 125
Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Ile Thr Leu Val Asp
            180

<210> SEQ ID NO 18
<211> LENGTH: 183
<212> TYPE: PRT
<213> ORGANISM: Neisseria meningitidis

<400> SEQUENCE: 18

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Glu Ala Thr Pro Ala
                20                  25                  30

Ala Glu Ala Pro Ala Ser Glu Ala Pro Ala Glu Ala Ala Pro Ala
            35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 19
<211> LENGTH: 183
<212> TYPE: PRT
<213> ORGANISM: Neisseria meningitidis

<400> SEQUENCE: 19

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Glu Ala Thr Pro Ala
                20                  25                  30

Ala Glu Ala Pro Ala Ser Glu Ala Pro Ala Glu Ala Ala Pro Ala
            35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
```

```
                65                   70                  75                  80
Ala Cys Lys Glu Phe Thr Ile Thr Leu Lys His Thr Gly Thr Gln Pro
                        85                  90                  95

Lys Thr Ser Met Gly His Asn Leu Val Ile Ala Lys Ala Glu Asp Met
                100                 105                 110

Asp Gly Val Phe Lys Asp Gly Val Gly Ala Ala Asp Thr Asp Tyr Val
                115                 120                 125

Lys Pro Asp Asp Ala Arg Val Val Ala His Thr Lys Leu Ile Gly Gly
130                 135                 140

Gly Glu Glu Ala Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
                180

<210> SEQ ID NO 20
<211> LENGTH: 201
<212> TYPE: PRT
<213> ORGANISM: Neisseria gonorrhoeae

<400> SEQUENCE: 20

Met His Phe Asp Phe Arg Lys Thr Glu Tyr Tyr Phe Ile Asp Trp Arg
1               5                   10                  15

Phe Thr Met Lys Ala Tyr Leu Ala Leu Ile Ser Ala Ala Val Ile Gly
                20                  25                  30

Leu Ala Ala Cys Ser Gln Glu Pro Ala Ala Pro Ala Ala Glu Ala Thr
            35                  40                  45

Pro Ala Gly Glu Ala Pro Ala Ser Glu Ala Pro Ala Ala Glu Ala Ala
        50                  55                  60

Pro Ala Asp Ala Ala Glu Ala Pro Ala Ala Gly Asn Cys Ala Ala Thr
65                  70                  75                  80

Val Glu Ser Asn Asp Asn Met Gln Phe Asn Thr Lys Asp Ile Gln Val
                85                  90                  95

Ser Lys Ala Cys Lys Glu Phe Thr Ile Thr Leu Lys His Thr Gly Thr
            100                 105                 110

Gln Pro Lys Ala Ser Met Gly His Asn Leu Val Ile Ala Lys Ala Glu
        115                 120                 125

Asp Met Asp Gly Val Phe Lys Asp Gly Val Gly Ala Ala Asp Thr Asp
130                 135                 140

Tyr Val Lys Pro Asp Asp Ala Arg Val Val Ala His Thr Lys Leu Ile
145                 150                 155                 160

Gly Gly Gly Glu Glu Ser Ser Leu Thr Leu Asp Pro Ala Lys Leu Ala
                165                 170                 175

Asp Gly Asp Tyr Lys Phe Ala Cys Thr Phe Pro Gly His Gly Ala Leu
            180                 185                 190

Met Asn Gly Lys Val Thr Leu Val Asp
        195                 200

<210> SEQ ID NO 21
<211> LENGTH: 201
<212> TYPE: PRT
<213> ORGANISM: Neisseria meningitidis

<400> SEQUENCE: 21

Met His Phe Asp Phe Cys Lys Thr Glu Tyr Tyr Phe Ile Asp Trp Arg
```

```
                1               5                      10                     15
            Phe Val Met Lys Ala Tyr Leu Ala Leu Ile Ser Ala Ala Val Ile Gly
                            20                  25                  30
            Leu Ala Ala Cys Ser Gln Glu Pro Ala Ala Pro Ala Ala Glu Ala Thr
                            35                  40                  45
            Pro Ala Gly Glu Ala Pro Ala Ser Glu Ala Pro Ala Ala Glu Ala Ala
                            50                  55                  60
            Pro Ala Asp Ala Ala Glu Ala Pro Ala Ala Gly Asn Cys Ala Ala Thr
            65                      70                  75                  80
            Val Glu Ser Asn Asp Asn Met Gln Phe Asn Thr Lys Asp Ile Gln Val
                                85                  90                  95
            Ser Lys Ala Cys Lys Glu Phe Thr Ile Thr Leu Lys His Thr Gly Thr
                            100                 105                 110
            Gln Pro Lys Ala Ser Met Gly His Asn Leu Val Ile Ala Lys Ala Glu
                            115                 120                 125
            Asp Met Asp Gly Val Phe Lys Asp Gly Val Gly Ala Ala Asp Thr Asp
                            130                 135                 140
            Tyr Val Lys Pro Asp Asp Ala Arg Val Val Ala His Thr Lys Leu Ile
            145                     150                 155                 160
            Gly Gly Gly Glu Glu Ala Ser Leu Thr Leu Asp Pro Ala Lys Leu Ala
                                165                 170                 175
            Asp Gly Asp Tyr Lys Phe Ala Cys Thr Phe Pro Gly His Gly Ala Leu
                            180                 185                 190
            Met Asn Gly Lys Val Thr Leu Val Asp
                            195                 200

<210> SEQ ID NO 22
<211> LENGTH: 183
<212> TYPE: PRT
<213> ORGANISM: Neisseria gonorrhoeae

<400> SEQUENCE: 22

Met Lys Ala Tyr Leu Ala Leu Ile Ser Ala Ala Val Ile Gly Leu Ala
1               5                   10                  15
Ala Cys Ser Gln Glu Pro Ala Ala Pro Ala Ala Glu Ala Thr Pro Ala
                20                  25                  30
Gly Glu Ala Pro Ala Ser Glu Ala Pro Ala Ala Glu Ala Ala Pro Ala
            35                  40                  45
Asp Ala Ala Glu Ala Pro Ala Ala Gly Asn Cys Ala Ala Thr Val Glu
        50                  55                  60
Ser Asn Asp Asn Met Gln Phe Asn Thr Lys Asp Ile Gln Val Ser Lys
65                  70                  75                  80
Ala Cys Lys Glu Phe Thr Ile Thr Leu Lys His Thr Gly Thr Gln Pro
                85                  90                  95
Lys Ala Ser Met Gly His Asn Leu Val Ile Ala Lys Ala Glu Asp Met
            100                 105                 110
Asp Gly Val Phe Lys Asp Gly Val Gly Ala Ala Asp Thr Asp Tyr Val
        115                 120                 125
Lys Pro Gly Asp Ala Arg Val Val Ala His Thr Lys Leu Ile Gly Gly
    130                 135                 140
Gly Glu Glu Ser Ser Leu Thr Leu Asp Pro Ala Lys Leu Ala Asp Gly
145                 150                 155                 160
Asp Tyr Lys Phe Ala Cys Thr Phe Pro Gly His Gly Ala Leu Met Asn
                165                 170                 175
```

Gly Lys Val Thr Leu Val Asp
            180

<210> SEQ ID NO 23
<211> LENGTH: 183
<212> TYPE: PRT
<213> ORGANISM: Neisseria meningitidis

<400> SEQUENCE: 23

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Ala Glu Ala Pro Ala Ser Glu Ala Pro Ala Ala Glu Ala Ala Pro Ala
        35                  40                  45

Asp Ala Ala Glu Ala Pro Ala Val Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ala Ser Leu Thr Leu Asp Pro Ala Lys Leu Ala Asp Gly
145                 150                 155                 160

Glu Tyr Lys Phe Ala Cys Thr Phe Pro Gly His Gly Ala Leu Met Asn
                165                 170                 175

Gly Lys Val Thr Leu Val Asp
            180

<210> SEQ ID NO 24
<211> LENGTH: 183
<212> TYPE: PRT
<213> ORGANISM: Neisseria meningitidis

<400> SEQUENCE: 24

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
            20                  25                  30

Gly Glu Ala Pro Ala Ser Glu Ala Pro Ala Ala Glu Ala Ala Pro Ala
        35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
            130                 135                 140

Gly Glu Glu Ala Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180

<210> SEQ ID NO 25
<211> LENGTH: 183
<212> TYPE: PRT
<213> ORGANISM: Neisseria gonorrhoeae

<400> SEQUENCE: 25

Met Lys Ala Tyr Leu Ala Leu Ile Ser Ala Ala Val Ile Gly Leu Ala
1               5                   10                  15

Ala Cys Ser Gln Glu Pro Ala Ala Pro Ala Ala Glu Ala Thr Pro Ala
                20                  25                  30

Gly Glu Ala Pro Ala Ser Glu Ala Pro Ala Ala Glu Ala Ala Pro Ala
            35                  40                  45

Asp Ala Ala Glu Ala Pro Ala Ala Gly Asn Cys Ala Ala Thr Val Glu
    50                  55                  60

Ser Asn Asp Asn Met Gln Phe Asn Thr Lys Asp Ile Gln Val Ser Lys
65                  70                  75                  80

Ala Cys Lys Glu Phe Thr Ile Thr Leu Lys His Thr Gly Thr Gln Pro
                85                  90                  95

Lys Ala Ser Met Gly His Asn Leu Val Ile Ala Lys Ala Glu Asp Met
            100                 105                 110

Asp Gly Val Phe Lys Asp Gly Val Gly Ala Ala Asp Thr Asp Tyr Val
        115                 120                 125

Lys Pro Asp Asp Ala Arg Val Val Ala His Thr Lys Leu Ile Gly Gly
    130                 135                 140

Gly Glu Glu Ser Ser Leu Thr Leu Asp Pro Ala Lys Leu Ala Asp Gly
145                 150                 155                 160

Asp Tyr Lys Phe Ala Cys Thr Phe Pro Gly His Gly Ala Leu Met Asn
                165                 170                 175

Gly Lys Val Thr Leu Val Asp
            180

<210> SEQ ID NO 26
<211> LENGTH: 167
<212> TYPE: PRT
<213> ORGANISM: Neisseria

<400> SEQUENCE: 26

Met Ala Ser Gln Glu Pro Ala Ala Pro Ala Ala Glu Ala Thr Pro Ala
1               5                   10                  15

Gly Glu Ala Pro Ala Ser Glu Ala Pro Ala Ala Glu Ala Ala Pro Ala
                20                  25                  30

Asp Ala Ala Glu Ala Pro Ala Ala Gly Asn Cys Ala Ala Thr Val Glu
            35                  40                  45

Ser Asn Asp Asn Met Gln Phe Asn Thr Lys Asp Ile Gln Val Ser Lys
    50                  55                  60

Ala Cys Lys Glu Phe Thr Ile Thr Leu Lys His Thr Gly Thr Gln Pro
65                  70                  75                  80

-continued

```
Lys Ala Ser Met Gly His Asn Leu Val Ile Ala Lys Ala Glu Asp Met
                85                  90              95

Asp Gly Val Phe Lys Asp Gly Val Gly Ala Ala Asp Thr Asp Tyr Val
            100             105                 110

Lys Pro Asp Asp Ala Arg Val Val Ala His Thr Lys Leu Ile Gly Gly
        115                 120                 125

Gly Glu Glu Ser Ser Leu Thr Leu Asp Pro Ala Lys Leu Ala Asp Gly
        130             135              140

Asp Tyr Lys Phe Ala Cys Thr Phe Pro Gly His Gly Ala Leu Met Asn
145                 150                 155                 160

Gly Lys Val Thr Leu Val Asp
                165
```

UNITED STATES PATENT AND TRADEMARK OFFICE
CERTIFICATE OF CORRECTION

| | |
|---|---|
| PATENT NO. | : 11,136,613 B2 |
| APPLICATION NO. | : 15/570262 |
| DATED | : October 5, 2021 |
| INVENTOR(S) | : Davies et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this
Tenth Day of January, 2023

Katherine Kelly Vidal
*Director of the United States Patent and Trademark Office*